United States Patent
Becker et al.

(10) Patent No.: US 12,232,827 B2
(45) Date of Patent: *Feb. 25, 2025

(54) TECHNIQUES FOR PATIENT-SPECIFIC MILLING PATH GENERATION

(71) Applicant: MAKO Surgical Corp., Weston, FL (US)

(72) Inventors: Hans-Ulrich Becker, Muellheim (DE); Michael Dale Dozeman, Portage, MI (US); Michael Ferko, Warwick, NY (US); Gregory Garcia, Parkland, FL (US); Vladimir Gershuni, Brooklyn, NY (US); José Luis Moctezuma de la Barrera, Freiburg (DE); Mark Ellsworth Nadzadi, Batavia, OH (US); Patrick Roessler, Merzhausen (DE)

(73) Assignee: MAKO Surgical Corp., Weston, FL (US)

( * ) Notice: Subject to any disclaimer, the term of this patent is extended or adjusted under 35 U.S.C. 154(b) by 168 days.

This patent is subject to a terminal disclaimer.

(21) Appl. No.: 18/080,160

(22) Filed: Dec. 13, 2022

(65) Prior Publication Data

US 2023/0114040 A1    Apr. 13, 2023

Related U.S. Application Data

(63) Continuation of application No. 16/441,513, filed on Jun. 14, 2019, now Pat. No. 11,564,749.

(Continued)

(51) Int. Cl.
*A61B 34/20* (2016.01)
*A61B 17/16* (2006.01)

(Continued)

(52) U.S. Cl.
CPC .............. *A61B 34/20* (2016.02); *A61B 17/16* (2013.01); *A61B 34/10* (2016.02); *A61B 34/30* (2016.02);

(Continued)

(58) Field of Classification Search
CPC ......... A61B 34/20; A61B 34/10; A61B 34/70; A61B 17/16; G05B 19/40; G05B 19/4099
See application file for complete search history.

(56) References Cited

U.S. PATENT DOCUMENTS 8,936,596 B2 *   1/2015   Mittelstadt ............. G16H 20/40
                                                              606/86 R
9,008,757 B2     4/2015   Wu (Continued)

FOREIGN PATENT DOCUMENTS

EP          0890890 A1      1/1999
EP          1326150 A2      7/2003
WO       2016187399 A1     11/2016

*Primary Examiner* — Christopher J Beccia
(74) *Attorney, Agent, or Firm* — Howard & Howard Attorneys PLLC

(57) ABSTRACT

Surgical systems, computer-implemented methods, and software programs for generating a milling path for a bone. The implementations involve obtaining a virtual model of the bone, a resection volume defined relative to the virtual model of the bone, and a reference guide defined with respect to the resection volume. Section planes are successively arranged along the reference guide, and each section plane intersects the reference guide and intersects the resection volume. A section path is generated within each section plane and is defined relative to the resection volume. Transition segments are generated to connect section paths of section planes. The milling path is then generated by combining the section paths and the transition segments.

32 Claims, 12 Drawing Sheets

Related U.S. Application Data

(60) Provisional application No. 62/685,476, filed on Jun. 15, 2018.

(51) Int. Cl.
*A61B 34/00* (2016.01)
*A61B 34/10* (2016.01)
*A61B 34/30* (2016.01)

(52) U.S. Cl.
CPC ...... *A61B 34/70* (2016.02); *A61B 2017/1602* (2013.01); *A61B 2034/101* (2016.02); *A61B 2034/107* (2016.02); *A61B 2034/2051* (2016.02); *A61B 2034/2063* (2016.02); *A61B 2034/2065* (2016.02)

(56) References Cited

U.S. PATENT DOCUMENTS

| | | |
|---|---|---|
| 9,119,655 B2 | 9/2015 | Bowling et al. |
| 9,480,534 B2 | 11/2016 | Bowling et al. |
| 11,564,749 B2 * | 1/2023 | Becker ............... A61B 34/30 |
| 2002/0002420 A1 | 1/2002 | Hirai et al. |
| 2003/0120375 A1 * | 6/2003 | Arai ................ G05B 19/4097 |
| | | 700/172 |
| 2012/0330429 A1 | 12/2012 | Axelson, Jr. et al. |
| 2014/0244220 A1 * | 8/2014 | McKinnon ............. A61F 2/02 |
| | | 703/1 |
| 2014/0276949 A1 | 9/2014 | Staunton et al. |
| 2015/0080717 A1 | 3/2015 | Ferko |
| 2016/0038243 A1 | 2/2016 | Miller et al. |
| 2016/0296296 A1 | 10/2016 | Bowling et al. |
| 2016/0338782 A1 | 11/2016 | Bowling et al. |
| 2017/0000572 A1 | 1/2017 | Moctezuma de la Barrera et al. |
| 2019/0380788 A1 | 12/2019 | Becker et al. |

* cited by examiner

TECHNIQUES FOR PATIENT-SPECIFIC MILLING PATH GENERATION

CROSS-REFERENCE TO RELATED APPLICATIONS

The subject application is a continuation of U.S. patent application Ser. No. 16/441,513, filed on Jun. 14, 2019, which claims priority to and all the benefits of U.S. Provisional Patent App. No. 62/685,476, filed Jun. 15, 2018, the entire contents of each of the aforementioned applications being hereby incorporated by reference.

TECHNICAL FIELD

The present disclosure relates generally to techniques for generating a milling path for a tool of a surgical system.

BACKGROUND

Robotic systems are commonly used to perform surgical procedures and typically include a robot comprising a robotic arm and an end effector coupled to an end of the robotic arm. Often, the end effector comprises a shaft with a milling burr coupled to the distal end of the shaft.

In a manual mode of operation, the robotic system senses forces/torques manually applied to the end effector by the user. The robotic system commands positioning of end effector to emulate motion expected from application of the sensed forces/torques. In fully autonomous or semi-autonomous modes, the robotic system commands the robot arm to move the end effector along a computer-defined milling path at least partially unassisted by the user. In either mode, a supplemental tracking system, such as optical localization, may be utilized to track positioning of the robot and the surgical site.

Conventionally, the milling path is utilized to remove a resection volume of the anatomy to accommodate insertion of a surgical implant. Although prior techniques adequately remove the anatomy of the resection volume, there are several technical problems associated with the milling planning and execution.

For instance, prior techniques often generate milling paths where the overall path length and milling time are increased. In turn, prior techniques exhibit reduced efficiency and suboptimal run-time behavior.

Moreover, conventional milling paths are not constrained to the hard tissue (e.g., bone). For the legacy method, the path is computed prior to knowing the desired implant placement in relation to the bone, i.e., the path is implant specific and does not take into account the hard tissue boundaries in relation to the implant. Implant specific paths hence need to be designed for the allowable worst case placement (i.e., that of greatest potential bone removal), thus resulting in additional path length not needed for the typical case. Hence, prior approaches, i.e., "implant specific, worst case" milling paths, remove more material than is needed for implant insertion. For example, prior milling paths perform "air-cutting" whereby the end effector is activated, but not engaging the bone. Milling in this fashion causes potential removal of surrounding tissue beyond the intended resection volume. For these reasons, prior techniques are not entirely "patient specific". Such issues are particularly evident in situations where the implant is an onlay/overhang type whereby the implant is located on top of the bone (not placed into depressions of the bone) and partially hangs over the edge of the bone. In such situations, adjacent soft tissue surrounds the overhang region making milling particularly challenging. For example, when intending to machine in a region of restricted access, such as machining posterior femur knee anatomy with the tibia bone nearby, worst-case paths may remove more of the femur bone than necessary. This air-cutting increases the possibility of the end effector shaft colliding with the nearby tibia bone.

Prior techniques also are limited to pre-operative generation of the milling path, thereby providing little flexibility to make intra-operative modifications to the resection volume and corresponding milling path. Thus, the surgeon would not be able to make intra-operative positioning adjustments to the location of the implant because conventional techniques are not equipped to adjust the resection volume and the milling path on-the-fly. Also undesirable is a situation wherein the path is designed for worst-case implant placement. In this case, the user can adjust the implant, but the path length is sub-optimal since it has been designed for the worst-case bone removal situation. The predefined worst-case path must be used since conventional techniques are not equipped to generate an adjusted milling path on-the-fly.

Furthermore, prior techniques utilize rudimentary linear segments for leading into the main milling path and leading out of the main milling path. Such entry and exit segments can cause unwanted plunge cuts into the anatomy because they abruptly enter the bone with excessive cut depth, rather than smoothly transitioning into the cut.

As such, there is a need in the art for systems and methods for addressing at least the aforementioned problems.

SUMMARY

This Summary introduces a selection of concepts in a simplified form that are further described below in the Detailed Description below. This Summary is not intended to limit the scope of the claimed subject matter, and does not necessarily identify each and every key or essential feature of the claimed subject matter.

According to a first aspect, a computer-implemented method is provided for generating a milling path for a bone, the computer-implemented method comprising: obtaining a virtual model of the bone, a resection volume defined relative to the virtual model of the bone, and a reference guide defined with respect to the resection volume; producing a plurality of section planes being successively arranged along the reference guide, and each section plane intersecting the reference guide and intersecting the resection volume; generating a section path within each section plane and being defined relative to the resection volume; generating transition segments for connecting section paths of section planes; and combining the section paths and the transition segments to generate the milling path.

According to a second aspect, a non-transitory computer readable medium is provided, comprising instructions being executable by one or more processors to generate a milling path for a bone, the instructions, when executed, are configured to: obtain a virtual model of the bone, a resection volume defined relative to the virtual model of the bone, and a reference guide defined with respect to the resection volume; produce a plurality of section planes successively arranged along the reference guide, and each section plane intersects the reference guide and intersects the resection volume; generate a section path within each section plane and defined relative to the resection volume; generate transition segments to connect section paths of section planes; and combine the section paths and the transition segments to generate the milling path.

According to a third aspect, a surgical system is provided comprising: a robotic manipulator configured to support and move a cutting tool relative to a bone; a control system coupled to the robotic manipulator and being configured to: generate a milling path for the cutting tool to enable the cutting tool to remove material from the bone, wherein to generate the milling path, the control system is configured to: obtain a virtual model of the bone, a resection volume defined relative to the virtual model of the bone, and a reference guide defined with respect to the resection volume; produce a plurality of section planes being successively arranged along the reference guide, and each section plane intersects the reference guide and intersects the resection volume; generate a section path within each section plane and being defined relative to the resection volume; generate transition segments to connect section paths of section planes; and combine the section paths and the transition segments; and the control system is configured to command the robotic manipulator to move the cutting tool along the generated milling path to remove the material from the bone.

Further provided is a method for operating the tool of the surgical system relative to the milling path of any of the examples described herein. The method includes moving the tool along the milling path and removing the resection volume with the tool. Also provided is a robotic surgical system comprising the one or more processors, the non-transitory computer readable medium, and software program of any example described herein, and wherein the robotic surgical system further comprises a tool that is configured to move relative to the milling path to remove the resection volume.

The system, method and software program provide technical solutions to several technical problems associated with conventional milling planning and execution.

For example, the milling path is generated using section paths interconnected by transition segments. As such, a single pass machining procedure may be used to generate the milling path. Mainly, with a single pass method, a two-stage roughing-and-finishing operation can be avoided if desired. Depending on the anatomical and surgical approach, the techniques described herein can significantly reduce milling path length and resection time. In turn, the techniques described herein exhibit increased efficiency and improved run-time behavior. However, it should be appreciated that the techniques described herein could be used to create two-stage paths and that might be beneficial for certain preparation steps and/or implants.

The techniques described herein further define the planned milling path with section paths located along the reference guide such that the milling is constrained to the hard tissue (e.g., bone). Thus, the generated milling path is designed to avoid soft tissue adjacent to the resection volume and to not remove more material than is needed for implant insertion. The milling path is tailored to enable the tool to continuously engage the bone intended for resection and without affecting surrounding tissue beyond the resection volume. For these reasons, the system, method and software program provide a truly "patient specific" solution.

With this improved approach for generation of the milling path, a wide array of milling procedures can be executed with a high degree of accuracy. For instance, milling is possible for insertion of the onlay/overhang type implant as well as an inlay type implant (i.e., an implant that is inserted into a resected pocket of the bone and the implant is surrounded by a rim of bone). In the overhang region, the resection volume is reduced and the milling path is constrained to the resection volume such that surrounding soft tissue can be preserved.

Moreover, the techniques described herein reduce the likelihood of collision between the end effector shaft and the bone. For example, if milling is performed on the femur bone, collisions of the shaft with the tibia bone is avoided because only the minimal required amount of the femur bone is removed, thus avoiding the interaction with the nearby tibia bone possible in non-patient specific milling approaches.

While the system, method and software program enable pre-operative generation of the milling path, the solution further enables intra-operative generation of the milling path. The techniques described herein provide flexibility to make intra-operative modifications to the implant placement, and thus the resection volume and corresponding milling path. The surgeon can freely make positioning adjustments to the location of the implant because the software program is configured to generate an adjusted resection volume and an adjusted milling path intra-operatively and on-demand or as needed.

Furthermore, the techniques described herein are configured to generate transitional milling path segments that are optimized to reduce burr chatter, avoid unwanted outcomes (such as plunge cuts, or overly aggressive material removal), and improve overall quality of milling.

The system, method, and software program may exhibit advantages and provide technical solutions other than those described herein.

DESCRIPTION OF THE DRAWINGS

Advantages of the present invention will be readily appreciated as the same becomes better understood by reference to the following detailed description when considered in connection with the accompanying drawings wherein.

DETAILED DESCRIPTION

I. Overview of the Robotic Surgical System

Referring to the FIGS. 1 and 2, wherein like numerals indicate like or corresponding parts throughout the several views, a robotic surgical system 10 (hereinafter "system") and components thereof are illustrated. Further provided is a non-transitory computer readable medium comprising instructions, which when executed by one or more processors implement a software program for the robotic surgical system 10 as well as methods for using the software program. Aspects of the software program and method, and details surrounding the various algorithms involved with each computer implemented step are addressed in the subsequent section below.

Figure 1:
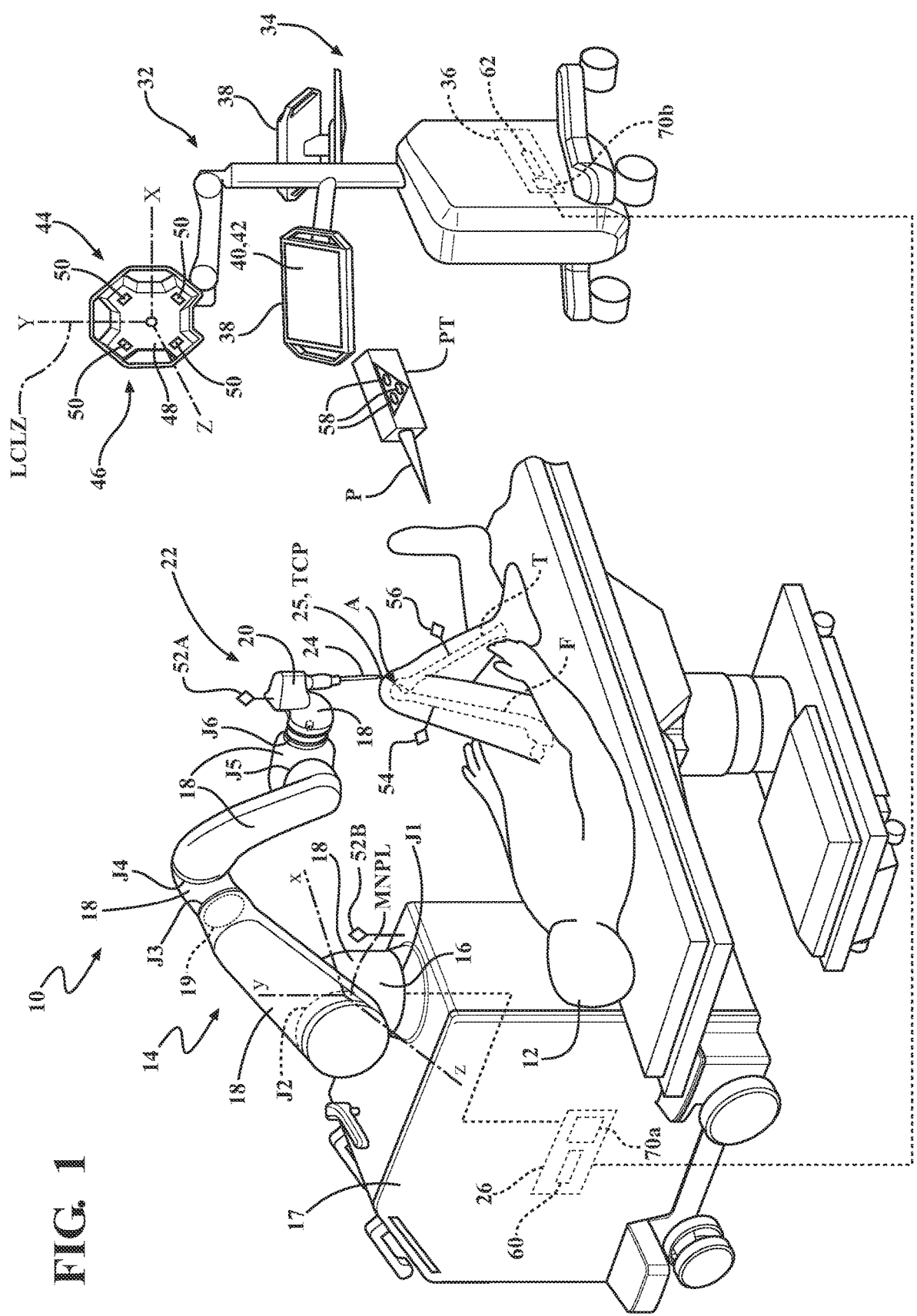
FIG. 1 is a perspective view of a robotic surgical system for manipulating a target tissue of a patient with a tool, according to one example

As shown in FIG. 1, the system 10 is a robotic surgical system for treating surgical site or anatomical volume (A) of a patient 12, such as bone or soft tissue. In FIG. 1, the patient 12 is undergoing a surgical procedure. The anatomy in FIG. 1 includes a femur (F) and a tibia (T) of the patient 12. The surgical procedure may involve tissue removal or treatment. Treatment may include cutting, coagulating, lesioning the tissue, treatment in place of tissue, or the like. In some examples, the surgical procedure involves partial or total knee or hip replacement surgery. In one example, the system 10 is designed to cut away material to be replaced by surgical implants, such as hip and knee implants, including unicompartmental, bicompartmental, multicompartmental, or total knee implants. Some of these types of implants are shown in U.S. Patent Application Publication No. 2012/0030429, entitled, "Prosthetic Implant and Method of Implantation," the disclosure of which is hereby incorporated by reference. The system 10 and techniques disclosed herein may be used to perform other procedures, surgical or non-surgical, or may be used in industrial applications or other applications where robotic systems are utilized.

The system 10 includes a manipulator 14. The manipulator 14 has a base 16 and plurality of links 18. A manipulator cart 17 supports the manipulator 14 such that the manipulator 14 is fixed to the manipulator cart 17. The links 18 collectively form one or more arms of the manipulator 14. The manipulator 14 may have a serial arm configuration (as shown in FIG. 1), a parallel arm configuration, or any other suitable manipulator configuration. In other examples, more than one manipulator 14 may be utilized in a multiple arm configuration.

In the example shown in FIG. 1, the manipulator 14 comprises a plurality of joints (J) and a plurality of joint encoders 19 located at the joints (J) for determining position data of the joints (J). For simplicity, only one joint encoder 19 is illustrated in FIG. 1, although other joint encoders 19 may be similarly illustrated. The manipulator 14 according to one example has six joints (J1-J6) implementing at least six-degrees of freedom (DOF) for the manipulator 14. However, the manipulator 14 may have any number of degrees of freedom and may have any suitable number of joints (J) and redundant joints (J).

The manipulator 14 need not require 'joint' encoders 19 but may alternatively or additionally utilize motor encoders. Also, the manipulator 14 need not require rotary joints, but may alternatively or additionally utilize one or more prismatic joints.

The base 16 of the manipulator 14 is generally a portion of the manipulator 14 that is stationary during usage thereby providing a fixed reference coordinate system (i.e., a virtual zero pose) for other components of the manipulator 14 or the system 10 in general. Generally, the origin of a manipulator coordinate system MNPL is defined at the fixed reference of the base 16. The base 16 may be defined with respect to any suitable portion of the manipulator 14, such as one or more of the links 18. Alternatively, or additionally, the base 16 may be defined with respect to the manipulator cart 17, such as where the manipulator 14 is physically attached to the cart 17. In one example, the base 16 is defined at an intersection of the axes of joints J1 and J2. Thus, although joints J1 and J2 are moving components in reality, the intersection of the axes of joints J1 and J2 is nevertheless a virtual fixed reference pose, which provides both a fixed position and orientation reference and which does not move relative to the manipulator 14 and/or cart 17. The manipulator 14 and/or manipulator cart 17 house a manipulator computer 26, or other type of control unit. In other examples, the manipulator 14 can be a hand-held where the base 16 is a portion of the tool 20 held stable while the tool tip follows the path.

A surgical tool 20 (hereinafter "tool") couples to the manipulator 14 and is movable relative to the base 16 to interact with the anatomy in certain modes. The tool 20 is or forms part of an end effector 22 in certain embodiments. The tool 20 may be grasped by the operator. One exemplary arrangement of the manipulator 14 and the tool 20 is described in U.S. Pat. No. 9,119,655, entitled, "Surgical Manipulator Capable of Controlling a Surgical Tool in Multiple Modes," the disclosure of which is hereby incorporated by reference. The manipulator 14 and the tool 20 may be arranged in alternative configurations. The tool 20 can be like that shown in U.S. Patent Application Publication No. 2014/0276949, filed on Mar. 15, 2014, entitled, "End Effector of a Surgical Robotic Manipulator," hereby incorporated by reference.

The tool 20 includes an energy applicator 24 designed to contact and remove the tissue of the patient 12 at the surgical site. In one example, the energy applicator 24 is a burr 25. The burr 25 may be substantially spherical and comprise a spherical center, radius (r) and diameter. Alternatively, the energy applicator 24 may be a drill bit, a saw blade, an ultrasonic vibrating tip, or the like. The tool 20 and/or energy applicator 24 may comprise any geometric feature, e.g., perimeter, circumference, radius, diameter, width, length, volume, area, surface/plane, range of motion envelope (along any one or more axes), etc. As will be described below, the geometric feature may be considered in certain features relating to offsets from virtual constraints involved with how the tool path is calculated.

The tool 20 may comprise a tool center point (TCP), which in one example, is a predetermined reference point defined at the energy applicator 24. The TCP has a known, or able to be calculated (i.e., not necessarily static), pose relative to other coordinate systems of the manipulator 14. The geometry of the energy applicator 24 is known in or defined relative to the TCP coordinate system. The TCP may be located at the spherical center of the burr 25 of the tool 20 such that only one point is tracked. The TCP may be defined according to various manners depending on the configuration of the energy applicator 24. The manipulator 14 could have motor encoders, or any other non-encoder position sensing method, to enable pose of the TCP can be determined. The manipulator 14 may use joint measurements to determine TCP pose and/or could employ techniques to measure TCP pose directly. The control of the tool 20 is not limited to a center point. For example, any suitable primitives, meshes, etc., can be used to represent the tool 20.

Figure 2:
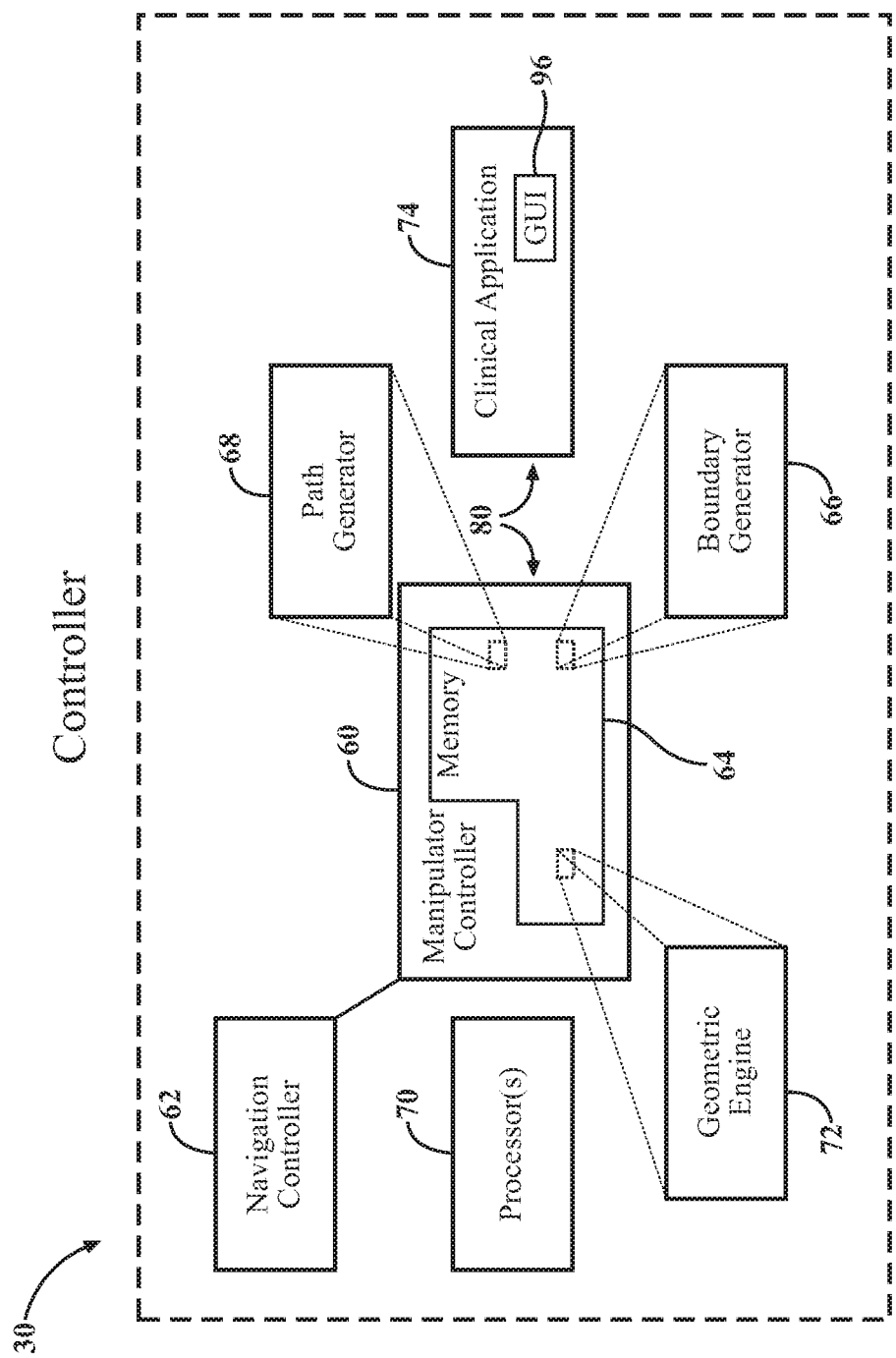
FIG. 2 is a block diagram of a controller for controlling the robotic surgical system, according to one example.

Referring to FIG. 2, the system 10 includes a controller 30. The controller 30 includes software and/or hardware for controlling the manipulator 14. The controller 30 directs the motion of the manipulator 14 and controls a state (position and/or orientation) of the tool 20 with respect to a coordinate system. The controller 30 can control (linear or angular) velocity, acceleration, or other derivatives of motion of the tool 20. In one example, the coordinate system is the manipulator coordinate system MNPL, as shown in FIG. 1. One example of the manipulator coordinate system MNPL is described in U.S. Pat. No. 9,119,655, entitled, "Surgical Manipulator Capable of Controlling a Surgical Tool in Multiple Modes," the disclosure of which is hereby incorporated by reference. Further aspects and capabilities of the controller 30 are described below.

The system 10 further includes a navigation system 32. One example of the navigation system 32 is described in U.S. Pat. No. 9,008,757, filed on Sep. 24, 2013, entitled, "Navigation System Including Optical and Non-Optical Sensors," hereby incorporated by reference. The navigation system 32 is configured to track movement of various objects. Such objects include, for example, the manipulator 14, the tool 20 and the anatomy, e.g., femur F and tibia T. The navigation system 32 tracks these objects to gather state information of each object with respect to a (navigation) localizer coordinate system LCLZ. Coordinates in the localizer coordinate system LCLZ may be transformed to the manipulator coordinate system MNPL, and/or vice-versa, using transformations.

The navigation system 32 includes a cart assembly 34 that houses a navigation computer 36, and/or other types of control units. A navigation interface is in operative communication with the navigation computer 36. The navigation interface includes one or more displays 38. The navigation system 32 is capable of displaying a graphical representation of the relative states of the tracked objects to the operator using the one or more displays 38. One or more input devices 40, 42 may be used to input information into the navigation computer 36 or otherwise to select/control certain aspects of the navigation computer 36. As shown in FIG. 1, such input devices 40, 42 include interactive touchscreen displays. However, the input devices 40, 42 may include any one or more of a keyboard, a mouse, a microphone (voice-activation), gesture control devices, and the like. The controller 30 may be implemented on any suitable device or devices in the system 10, including, but not limited to, the manipulator computer 26, the navigation computer 36, and any combination thereof.

The navigation system 32 also includes a navigation localizer 44 (hereinafter "localizer") coupled to the navigation computer 36. In one example, the localizer 44 is an optical localizer and includes a camera unit 46. The camera unit 46 has an outer casing 48 that houses one or more optical sensors 50.

The navigation system 32 includes one or more trackers. In one example, the trackers include a pointer tracker PT, one or more manipulator trackers 52, a first patient tracker 54, and a second patient tracker 56. In the illustrated example of FIG. 1, the manipulator tracker 52 is firmly attached to the tool 20 (i.e., tracker 52A), the first patient tracker 54 is firmly affixed to the femur F of the patient 12, and the second patient tracker 56 is firmly affixed to the tibia T of the patient 12. In this example, the patient trackers 54, 56 are firmly affixed to sections of bone. The pointer tracker PT is firmly affixed to a pointer P used for registering the anatomy to the localizer coordinate system LCLZ. The manipulator tracker 52 may be affixed to any suitable component of the manipulator 14, in addition to, or other than the tool 20, such as the base 16 (i.e., tracker 52B), or any one or more links 18 of the manipulator 14. The trackers 52, 54, 56, PT may be fixed to their respective components in any suitable manner. For example, the trackers may be rigidly fixed, flexibly connected (optical fiber), or not physically connected at all (ultrasound), as long as there is a suitable (supplemental) way to determine the relationship (measurement) of that respective tracker to the item that it is associated with.

Any one or more of the trackers may include active markers 58. The active markers 58 may include light emitting diodes (LEDs). Alternatively, the trackers 52, 54, 56 may have passive markers, such as reflectors, which reflect light emitted from the camera unit 46. Other suitable markers not specifically described herein may be utilized.

The localizer 44 tracks the trackers 52, 54, 56 to determine a state of each of the trackers 52, 54, 56, which correspond respectively to the state of the object respectively attached thereto. The localizer 44 provides the state of the trackers 52, 54, 56 to the navigation computer 36. In one example, the navigation computer 36 determines and communicates the state the trackers 52, 54, 56 to the manipulator computer 26. As used herein, the state of an object includes, but is not limited to, data that defines the position and/or orientation of the tracked object or equivalents/derivatives of the position and/or orientation. For example, the state may be a pose of the object, and may include linear velocity data, and/or angular velocity data, and the like.

Although one example of the navigation system 32 is shown in the Figures, the navigation system 32 may have any other suitable configuration for tracking the manipulator 14 and the patient 12. In another example, the navigation system 32 and/or localizer 44 are ultrasound-based. For example, the navigation system 32 may comprise an ultrasound imaging device coupled to the navigation computer 36. The ultrasound imaging device images any of the aforementioned objects, e.g., the manipulator 14 and the patient 12, and generates state signals to the controller 30 based on the ultrasound images. The ultrasound images may be 2-D, 3-D, or a combination of both. The navigation computer 36 may process the images in near real-time to determine states of the objects. The ultrasound imaging device may have any suitable configuration and may be different than the camera unit 46 as shown in FIG. 1.

In another example, the navigation system 32 and/or localizer 44 are radio frequency (RF)-based. For example, the navigation system 32 may comprise an RF transceiver coupled to the navigation computer 36. The manipulator 14 and the patient 12 may comprise RF emitters or transponders attached thereto. The RF emitters or transponders may be passive or actively energized. The RF transceiver transmits an RF tracking signal and generates state signals to the controller 30 based on RF signals received from the RF emitters. The navigation computer 36 and/or the controller 30 may analyze the received RF signals to associate relative states thereto. The RF signals may be of any suitable frequency. The RF transceiver may be positioned at any suitable location to track the objects using RF signals effectively. Furthermore, the RF emitters or transponders may have any suitable structural configuration that may be much different than the trackers 52, 54, 56 as shown in FIG. 1.

In yet another example, the navigation system 32 and/or localizer 44 are electromagnetically based. For example, the navigation system 32 may comprise an EM transceiver coupled to the navigation computer 36. The manipulator 14 and the patient 12 may comprise EM components attached thereto, such as any suitable magnetic tracker, electromagnetic tracker, inductive tracker, or the like. The trackers may be passive or actively energized. The EM transceiver generates an EM field and generates state signals to the controller 30 based upon EM signals received from the trackers. The navigation computer 36 and/or the controller 30 may analyze the received EM signals to associate relative states thereto. Again, such navigation system 32 examples may have structural configurations that are different than the navigation system 32 configuration as shown throughout the Figures.

The navigation system 32 and/or localizer 44 may have any other suitable components or structure not specifically recited herein. Furthermore, any of the techniques, methods, and/or components described above with respect to the camera-based navigation system 32 shown throughout the Figures may be implemented or provided for any of the other examples of the navigation system 32 described herein. For example, the navigation system 32 may utilize solely inertial tracking or any combination of tracking techniques.

As shown in FIG. 2, the controller 30 further includes one or more software programs and software modules. The software modules may be part of the program or programs that operate on the manipulator computer 26, navigation computer 36, or a combination thereof, to process data to assist with control of the system 10. The software programs and/or modules includes computer readable instructions stored in non-transitory memory 64 on the manipulator computer 26, navigation computer 36, or a combination thereof, to be executed by one or more processors 70a, 70b of the computers 26, 36. The memory 64 may be any suitable configuration of memory, such as RAM, non-volatile memory, etc., and may be implemented locally or from a remote database. Additionally, software modules for prompting and/or communicating with the operator may form part of the program or programs and may include instructions stored in memory 64 on the manipulator computer 26, navigation computer 36, or a combination thereof. The operator may interact with any of the input devices 40, 42 and the displays 38 to communicate with the software modules. The user interface software may run on a separate device from the manipulator computer 26 and navigation computer 36.

The controller 30 includes a manipulator controller 60 for processing data to direct motion of the manipulator 14. In one example, as shown in FIG. 1, the manipulator controller is implemented on the manipulator computer 26. The controller 30 further includes a navigation (or localization) controller 62 for communicating the state data relating to the femur F, tibia T, and manipulator 14 to the manipulator controller 60. The navigation controller 62 is also configured to process/analyze the measurements from the camera and trackers to compute the state data. This processing could be done elsewhere on the system, including inside the camera itself. The manipulator controller 60 receives and processes the state data provided by the navigation controller 62 to direct movement of the manipulator 14. As shown in FIG. 1, the navigation controller 62 is implemented on the navigation computer 36. The controllers 60 and 62 handle the real-time control and algorithms.

As shown in FIG. 2, the controller 30 includes a boundary generator 66. The boundary generator 66 is a software program or module that generates a planar or non-planar virtual boundary 70 for constraining movement and/or operation of the tool 20. Such virtual boundaries 70 may also be referred to as virtual meshes, virtual constraints, or the like. The virtual boundaries 70 may be defined with respect to an anatomical model, such as a 3-D bone model. The anatomical model (AM) is registered to the one or more patient trackers 54, 56 such that the virtual boundaries 70 become associated with to the anatomical model (AM). The manipulator controller 60 executes the virtual boundaries 70 by tracking the state of the tool 20 relative to the virtual boundaries 70. In one example, the state of the TCP is measured relative to the virtual boundaries 70 for purposes of determining haptic forces that are applied to a virtual model via a physics simulation. The results of the simulation are commanded to the manipulator 14. The controller 30 controls/positions the manipulator 14 in a manner that emulates the way a physical handpiece would respond to the user and virtual haptic forces. The boundary generator 66 may be implemented on the manipulator controller 60. Alternatively, the boundary generator 66 may be implemented on other components, such as the navigation controller 62.

The virtual boundaries 70 can be either implant-specific or patient-specific. Thus, it is not necessary to have patient-specific virtual boundaries 70 even for the case of patient-specific tool paths. For implant-specific scenarios, the boundary generator 66 does not need to be part of the system 10 or controller 30, but rather the boundaries 70 can be manually generated offline for each possible implant size, and the resulting boundaries 70 stored with the software. For patient-specific scenarios, the boundary generator 66 may be part of a clinical application 74 (described below) that handles user interaction, rather than part of the controller 30 or manipulator controller 60.

A milling path generator 68 is another software program or module run by the controller 30. In one example, the milling path generator 68 is run by the manipulator controller 60. The milling path generator 68 generates a milling path 100 for the tool 20 to traverse, such as for removing sections of the anatomy to receive an implant.

It should be understood that the term "milling path" generally refers to the path of the tool 20 in the vicinity of the target site for milling the anatomy and is not intended to require that the tool 20 be operably milling the anatomy throughout the entire duration of the path. For instance, and as will be understood in further detail below, the milling path 100 may comprise sections or segments where the tool 20 transitions from one location to another without executing milling.

A geometric engine 72 is another software program or module run by the controller 30. The geometric engine 72 may be a sub-set of the milling path generator 68 or may be a program or module separate from the milling path generator 68. The geometric engine 72 is configured to assist in milling path 100 generation as well as providing on-the-fly flexibility for accommodating intra-operative changes to the surgical plan, e.g., implant placement. The geometric engine 72 will be described in detail below.

The boundary generator 66, milling path generator 68, and geometric engine 72 may be sub-sets of a software program 80. Alternatively, each may be software programs that operate separately and/or independently in any combination thereof. The term "software program" is used herein to describe the computer-executable instructions that are configured to carry out the various capabilities of the technical solutions described. For simplicity, the term "software program" is intended to encompass, at least, any one or more of the boundary generator 66, milling path generator 68, and/or geometric engine 72. The software program 80 can be implemented on the manipulator controller 60, navigation controller 62, or combination thereof.

One example of a system and method for generating the milling path 100 is explained in U.S. Pat. No. 9,119,655, entitled, "Surgical Manipulator Capable of Controlling a Surgical Tool in Multiple Modes," the disclosure of which is hereby incorporated by reference. In some examples, the virtual boundaries 70 and/or milling paths 100 may be generated offline rather than on the manipulator computer 26 or navigation computer 36. Thereafter, the virtual boundaries 70 and/or milling paths 100 may be utilized at runtime by the manipulator controller 60.

A clinical application 74 is provided to handle the user interaction. The clinical application 74 handles many aspects of user interaction and coordinates the surgical workflow, including pre-operative planning, implant placement, registration, bone preparation visualization, and post-operative evaluation of implant fit, etc. The clinical application 74 is configured to output to the displays 38. The clinical application 74 either may run on its own separate processor or may run alongside controller 62 on the navigation computer 36. In one example, the clinical application 74 interfaces with the path generator 68 and geometric engine 72 after implant placement is set by the user, and then sends the tool path returned by the path generator 68 to controller 60 for execution. Manipulator controller 60 executes a tool path as described herein. The manipulator controller 60 may create certain segments (e.g., lead-in segments) when starting or resuming machining to smoothly get back to the generated tool path.

In the semi-autonomous mode, the input for the primary movement of the TCP for bone resection is based off the tool path. In the semi-autonomous mode, the manipulator 14 is capable of moving the tool 20 free of operator assistance. Free of operator assistance may mean that an operator is not required to physically contact the tool 20 to apply force to move the tool 20. Instead, the operator may use some form of control to remotely manage starting and stopping of movement. For example, the operator may hold down a button of a remote control to start movement of the tool 20 and release the button to stop movement of the tool 20. Alternatively, the operator may press a button to start movement of the tool 20 and press a button to stop movement of the tool 20. In some modes of operation, the tool path automatically advances the TCP position, but the orientation of the tool 20 can be adjusted by the user by physically applying forces. The techniques described herein for tool path generation may still be used for this example to define the TCP positioning even though the user is contacting the tool 20 for reorientation. Moreover, even during semi-autonomous execution, boundary constraints may stay active as a risk mitigation against any issues/errors in the tool path. The operator could also vary speed and feed during the procedure to optimize the cutting. This could be done if tool chatter was detected.

Alternatively, the system 10 may be operated in the manual mode. In the manual mode, the input for the primary movement of the TCP for bone resection is based off the user-applied forces/torques. Here, the operator manually directs, and the manipulator 14 controls, movement of the tool 20 and, in turn, the energy applicator 24 at the surgical site. The operator physically contacts the tool 20 to cause movement of the tool 20. The manipulator 14 monitors the forces and torques placed on the tool 20 by the operator in order to position the tool 20. A sensor that is part of the manipulator 14, such as a force-torque transducer, measures these forces and torques. In response to the applied forces and torques, the manipulator 14 mechanically moves the tool 20 in a manner that emulates the movement that would have occurred based on the forces and torques applied by the operator. Movement of the tool 20 in the manual mode is also constrained in relation to the virtual constraints generated by the boundary generator 66 and/or path generator 68.

II. Milling Path Generation

Described herein are advanced techniques for generating the milling path 100 for the tool 20. Any of the techniques described herein can be implemented by the surgical system 10, methods implemented by the surgical system 10, and/or by the software program 80 executed by the surgical system 10. The software program 80 may be embodied by the clinical application 74 and/or the controller 30, or any part thereof. Steps of the computer-implemented method of executing these techniques can be understood through description below.

In summary, the milling path 100 is designed to remove a resection volume (RV) associated with the anatomical volume (A). The software program 80 defines a reference guide (G), such as a reference spline (RS), with respect to the resection volume (RV). The software program 80 defines, in succession, a plurality of sections (S) along the reference guide (G). Each section (S) intersects the reference guide (G) at a different intersection point (p). Each section (S) is at a specified orientation relative to the reference guide (G) at the intersection point (p). Furthermore, each section (S) intersects the resection volume (RV). The software program 80 generates a section path (SP) bounded within each section (S). Each section path (SP) is designed to remove a portion of the resection volume (RV). A plurality of transition segments (T) connect section paths (SP) of successive sections (S) along the reference guide (G). These features of the milling path 100 will be described in detail below.

The techniques described herein provide a 3D milling path 100 comprising an ordered sequence of lines or arcs. The milling path 100 is intended for or capable of completing resection via a single pass. In other words, a single milling path is defined for removal of the resection volume (RV) and the tool 20 can continuously remain on and remove material along the milling path 100 throughout the single pass. However, the path 100 may be utilized for any number of passes.

For illustrative purposes, the features are also described and shown for a partial knee arthroplasty for a femur distal case. Of course, the techniques and milling path 100 described herein may be utilized for anatomical resections other than those shown herein.

Furthermore, features are also described below with the assumption that the tool 20 comprises the spherical burr 25 as the energy applicator 24. Variations of the features below can are possible for energy applicators 24 other than a spherical burr 25.

A. Geometric Engine

With reference to FIG. 2, the geometric engine 72 is configured to compute and/or execute geometric operations that are needed to produce the milling path 100, or any part thereof. The path generator 68 produces the milling path 100, based in part, on the results or output of the geometric engine 72. The geometric engine 72 comprises a geometric modelling kernel, which is a 3D solid modeling software component.

Figure 3:
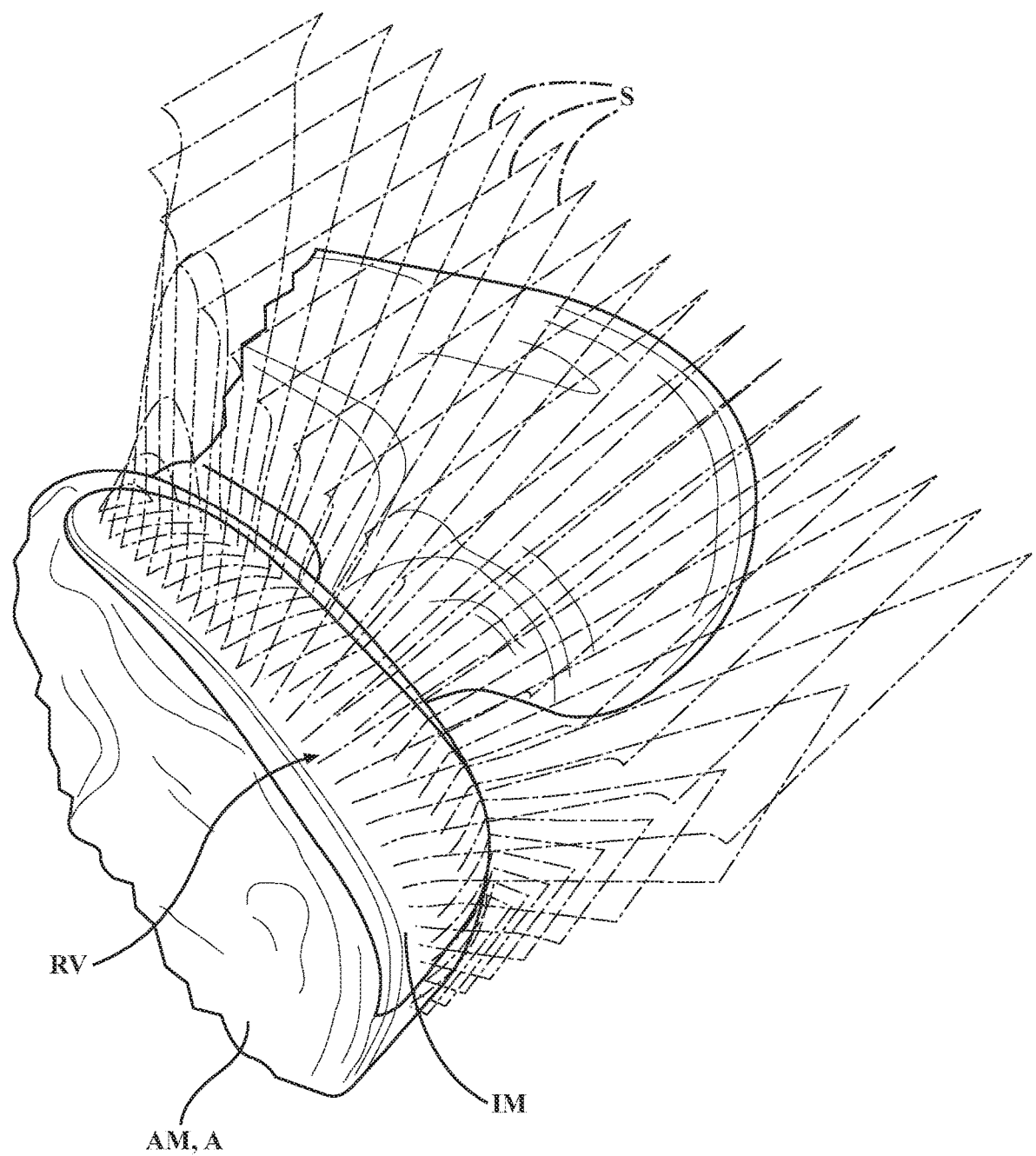
FIG. 3 is a perspective view of a computer-generated model of the anatomy (distal femur) shown with an implant model as well as geometric sections defined respectively thereto in preparation for planning a milling path for removal of a resection volume of the anatomy for receiving the physical implant.

With reference to FIG. 3, one input into the geometric engine 72 is an anatomical model (AM) of the anatomical volume (A). The anatomical model (AM) is a 3D virtual model of the anatomical volume (A), e.g., a bone, such as the femur, tibia, hip, etc. The anatomical model (AM) may be defined as a CAD model, mesh or any other volumetric image representation. In one example, the bone model is a mesh that is converted into a solid body model. The anatomical model (AM) may be generated in any file format, such as STL (Stereo Lithography) or VRML (Virtual Reality Modeling Language). The mesh may be derived from pre-operative imaging of the anatomical volume (A). The imaging modalities may be any one or more of CT, MRT, X-ray, Fluoro, MRI, and the like. These imaging modalities output slices that can be converted into the anatomical model (AM) through a process called segmentation. The anatomical model (AM) may be generated using any technique other than those described herein. The (AM) could be one or more surfaces and does not need to be a complete bone or tissue model.

Another input into the geometric engine 72 is an implant model (IM), as shown in FIG. 3. In FIG. 3, the implant model (IM) is shown in planned position on the anatomical model (AM). The implant model (IM) is a virtual 3D model of the physical implant that is intended for implantation into the anatomical volume (A). These models may be represented as 3D CAD solid bodies. The implant model (IM) may be any surgical implants, such as partial knee implants, including unicompartmental, bicompartmental, multicompartmental, total knee implants, spinal implants, hip implants, or the like.

The implant model (IM) can be selected from or otherwise derived from an electronic catalog of predefined implant models (IM). Implant selection is made such that the corresponding implant model (IM) adequately fits to the corresponding anatomical model (AM) in the region of implantation. Implant type and implant size selection is either made by and/or approved by the surgeon performing the procedure. This selection could be made pre-operatively and imported at the beginning of the procedure, and/or modified intra-operatively using the clinical application 74 shown on the displays 38 and by using one or more of the input devices 40, 42. The implant model (IM) could hold an entire plan or factors of the plan such as the reference guide (G). During use, the operator may specify changes or additions to finalize the path.

Additionally or alternatively, the implant model (IM) may be defined 'free-form' or 'drawn on-the-fly by the surgeon'. The implant model (IM) can be drawn, modeled, or adjusted by the surgeon using the input devices 40, 42 of the navigation system 32. In particular for these examples, the implant model (IM) may not necessarily represent a physical component to be installed into the bone, but rather represents a 'negative' of the desired bone/tissue to be removed. For such non-implant examples, it is also possible the 'non-implant' bone volume/shape to be removed comes from a pre-defined database or catalog, or calculated/suggested by the software or by a vendor-provided pre-operative plan. Hence, the 'non-implant' case is not limited to free-form or drawn on-the-fly examples.

In other applications, bone/tissue resection is being performed, but not necessarily for the primary purpose of receiving an implant. For this case, the implant model (IM) could be replaced with a solid model representative of the 'negative' of the bone/tissue to be removed. This solid model can be inputted into the geometric engine 72.

The geometric engine 72 is configured to load, store, manipulate, and/or create the anatomical model (AM). The geometric engine 72 may do so with or without visualization on the display 38.

The geometric engine 72 can also convert between all 3D representations utilized for the anatomical model (AM), thereby providing multimodal 3D model representation.

As will be described in detail below, the geometric engine 72 is further configured to compute intersections between the anatomical model (AM) and other objects, such as implant models, allowed volumes (AV), etc.

Another feature of the geometric engine 72 is the ability to perform 3D offset operations. Offset operations define a surface that is spaced apart from another surface by a predefined distance. One output of the offset operation is definition of the offset boundary, which is described below. The geometric engine 72 can also support offset operations for given planar or non-planar contours.

The geometric engine 72 may also compute planar sections for a 3D volume. One example of such sections are the sections (S) described herein.

Furthermore, the geometric engine 72 is configured to represent curves, such as polygons and spline curves. One example output of such features is generation of the reference guide (G), described herein. In addition, the geometric engine 72 can convert and/or approximate freeform curves into polygons, and vice versa. For example, this feature is helpful to facilitate forming of freeform implants or bone removal volumes.

Through these features and capabilities, the geometric engine 72 enables a patient-specific on-the-fly (intraoperative and near-real time) semi-Autonomous (or fully autonomous) generation of the milling path 100, even for freeform implants that are intraoperatively defined by the surgeon. Generation of the milling path 100 may be so spontaneous that milling by the tool 20 on generated portions of the milling path 100 takes place simultaneously while the geometric engine 72 is in the process of generating the remaining portions of the milling path 100.

As will be described below, on-the-fly generation of the resection volume (RV) is also possible. Additional capabilities of the geometric engine 72 will be understood from the description to follow. The geometric engine 72 may comprise features and capabilities other than those specifically described herein.

Any functionality described herein that is attributed to the geometric engine 72 may also be attributed to the path generator 68. The path generator 68 might have overall responsibility for the process of creating the path segments, connecting segments together, creating lead-ins, lead-outs, transitions, etc. The path generator 68 can make sub-calls to the geometric engine 72 for performing various geometric operations during the process.

B. Resection Volume

The resection volume (RV) is shown in FIGS. 3-6. The resection volume (RV) is a computer-defined volume of the anatomical volume (A) that is intended for removal by milling. In one example, the resection volume (RV) defines material of the anatomical volume (A) to be replaced by the physical implant. It should be appreciated that the implant, once installed, may only partially replace the resection volume (RV). More bone volume may need to be removed than the volume of the implant. For example, for the case in which the implant is placed deep into the bone (more than the thickness/depth of the implant), additional material would need to be removed to allow milling to take place down to the final implant surface. Furthermore, in certain cases, the resection volume (RV) may be defined for purposes other than for preparing the bone to receive a physical implant. Milling by the tool 20 is permitted in the resection volume (RV). The resection volume (RV) is patient or specimen specific.

The resection volume (RV) is defined directly or indirectly with reference to the anatomical model (AM). The resection volume (RV), when generated, may be stored by the geometric engine 72 or the clinical application 74. The resection volume (RV) can be sent to the manipulator controller 60 after the resulting tool path is generated and sent to the manipulator controller 60 for execution.

Once anatomical registration is performed using the navigation system 32, the anatomical model (AM) and corresponding resection volume (RV) become linked (e.g., spatially aligned) to the anatomical volume (A). This enables the manipulator controller 60 to control the tool 20 relative to the tracked anatomical volume (A) for removing the resection volume (RV).

Linking the anatomical model (AM) and corresponding resection volume (RV) may include several operations. For example, the image coordinate system and the anatomy coordinate system may be spatially aligned by selecting the key anatomical landmarks in the image (can be done offline). The image coordinate system and the tracker coordinate system may be spatially aligned by bone registration, i.e., by selecting points on the physical bone/tissue using the pointer to compute the relative location of the tracker mounted to the bone. The implant placement (its default location is defined relative to anatomy coordinate system) is then updated by the surgeon, defining its transform relative to the other coordinate systems (either image or anatomy). Hence, the relationship between the image, anatomy, and tracker coordinate systems becomes known. Then this result is combined with the registration result, so that the manipulator controller 60 can ultimately be given the resulting tool path along with a transform to relate it to the tracker coordinate system. The above process is handled by the clinical application 74. Then, the manipulator controller 60, by updating the movement of the manipulator 14 relative to the tracker in accordance with the tool path and provided transform, mills out the desired resection volume (RV) relative to the anatomy.

In one example, the resection volume (RV) is first defined with respect to the implant model (IM) in the implant coordinate system. The anatomical model (AM) may be understood as being in the image coordinate system. Once the relationship between the image and anatomy coordinate systems are known as specified above, then the anatomical volume (A) and anatomical model (AM) are 'linked' and this doesn't involve registration of the physical bone. The relationship between the anatomical model (AM) and an allowed volume (AV) (defined in implant coordinate system) becomes known following implant placement. The anatomical model (AM) is converted at this point into the implant coordinate system for the geometric Boolean (intersection) operations to take place. At this level in the processing, the location of the tracker and its relationship to the physical bone is not yet considered since that transform is applied downstream in the processing. The geometric operations, and ultimately the tool path generation, will be performed in implant coordinate system, and a transform will be computed using relationships between image, anatomy, tracker, and implant to give the manipulator controller 60 the relationship of the implant relative to tracker.

The resection volume (RV) may include one or more volumetric sections (components) that are separated or connected to one another. For example, these different components may define resection volumes (RV) for bicompartmental partial knee implants, or the like. The volumes separated from each other could also be part of the same compartment, e.g., unconnected 'islands' of material that need to be removed, that have resulted from the unique shape of the bone and the Boolean operations with the allowed volume.

In general, the resection volume (RV) is generated from intersection between two 3D CAD solid bodies. One of these solid bodies is the anatomical model (AM). The resection volume (RV) may be defined according to any one or more of the techniques, as described below.

1. Defined by Implant Model

The resection volume (RV) can be implant based. In one example, as shown in FIG. 3, the other solid body for defining the resection volume (RV) is implant model (IM). Here, the resection volume (RV) is defined by the volumetric intersection of the anatomical model (AM) and the implant model (IM). The software program 80, with assistance from the geometric engine 72, is configured to compute geometric interactions between the anatomical model (AM) and the implant model (IM) for defining the resection volume (RV). The resection volume (RV) can be shaped to the implant model (IM), while taking into account any designed interferences/clearances for fit.

2. Defined On-the-Fly

In another example, the other solid body for defining the resection volume (RV) is a solid body derived from ad-hoc intraoperative input. By virtue of the capabilities of the geometric engine 72, it is also possible to generate the resection volume (RV) intraoperatively or on-the-fly. For example, the surgeon may decide to change the pre-selected implant model (IM) intraoperatively. Alternatively, the surgeon may decide to abandon the preselected implant model (IM) altogether.

In either instance, the surgeon can create or modify a solid body for defining the resection volume (RV) other than the original implant model (IM). For example, the surgeon can use the input devices 40, 42 of the navigation system 32 to define parameters or landmarks for definition of the resection volume (RV). For example, the surgeon may define the resection volume (RV), partially or entirely, free-hand using the input devices 40, 42. Additionally or alternatively, the pointer P can be utilized for selecting or tracing the boundaries of the bone/tissue regions to be removed. The software program 80 can access the navigation data from the navigation system 32 and the geometric engine 72 can analyze the data and synthetize the resection volume (RV). The (RV) could have been partially resected by prior cutting. This could have been completed manually, by a previous smaller path, or a path that was interrupted.

Additionally or alternatively, the resection volume (RV) can be defined using any predefined solid bodies, primitive volumes, or any mathematically described surface or volume not described herein.

The resection volume (RV) can also be implant based and modified intra-operatively to match or adjust to the anatomic model (AM), such as by utilizing patient-specific morphing constraint techniques.

The resection volume (RV) can be surgeon defined. For example, the surgeon may desire a certain distance of interference or clearance between the implant and preparation surface. This can be defined via a preference or patient specific surgeon decision The resection volume (RV) can be automatically defined. For example, interference fit can be tailored based on a patient anatomical parameter such as bone density and/or elastic modulus for consistent effective interference fit, such as described in U.S. Patent Application Publication No. 20150080717A1, the disclosure of which is incorporated by reference in its entirely.

3. Defined By Protected Volume and/or Allowed Volumes

Figure 5:
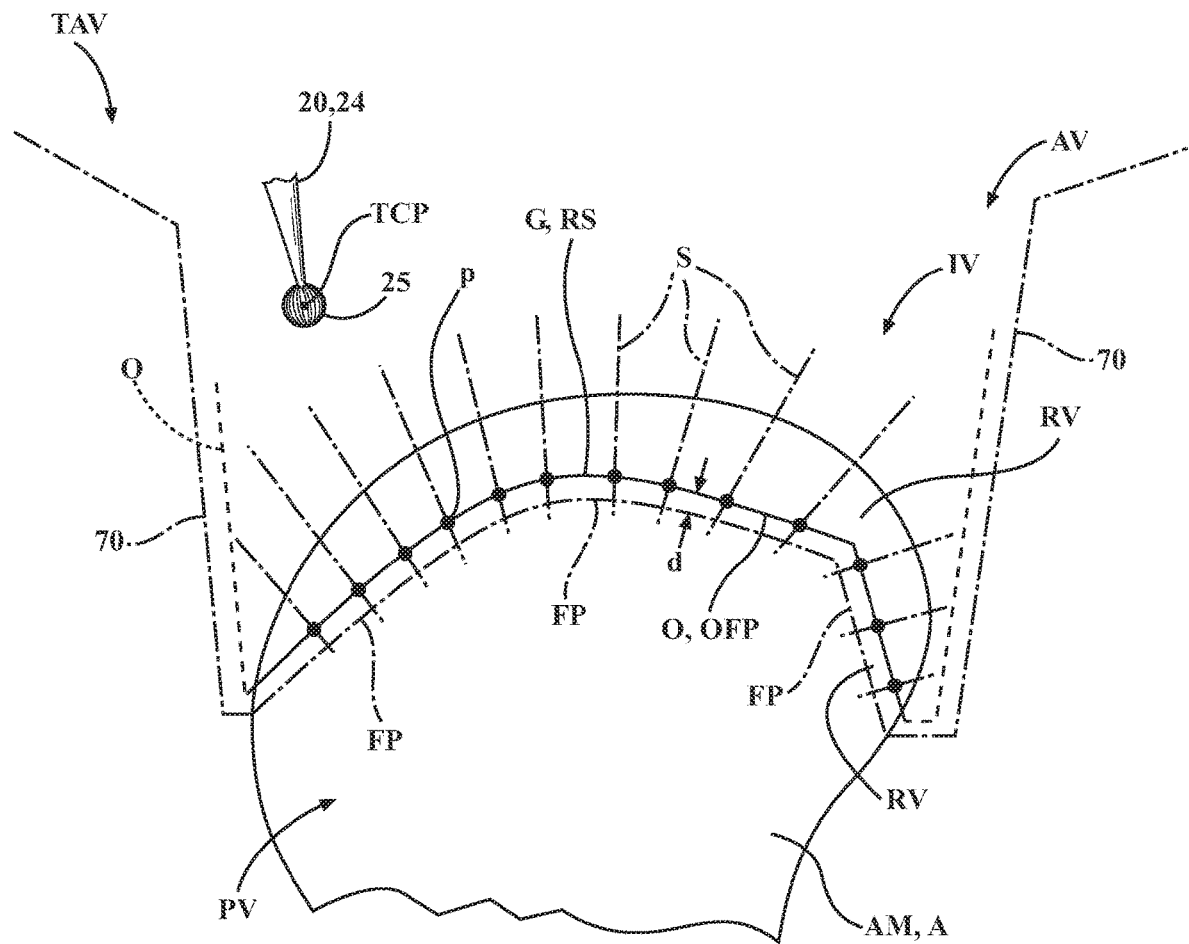
FIG. 5 is cross-sectional side view of the anatomical model having numerous geometric virtual features defined respectfully thereto for generation of the milling path.

To accompany (and at least partially define) the resection volume (RV), the software program 80 further is configured to define one or more protected volumes (PV), as shown in FIG. 5, for example. The protected volume (PV) is a 3D virtual region that may be associated with the implant model (IM). This way, when the surgeon changes the implant placement, the protected volume (PV) and/or resection volume (RV) moves relative to the anatomical model (AM) as well. When combined with the other transforms, the protected volume (PV) is ultimately known with respect to anatomical model (AM). Alternatively, the protected volume (PV) may be associated directly with the anatomical model (AM), and hence, includes a volumetric portion of the anatomical volume (A). The protected volume (PV) may additionally comprise regions in space that are beyond the anatomical volume (A).

The protected volume (PV) is a region of the anatomical volume (A) that should be protected from milling. In other words, milling by the tool 20 is prohibited in the protected volume (PV). In some instances, entry into the protected volume (PV) by the tool 20 is prohibited even if the tool 20 is not milling, e.g., in manual machining mode and/or when the energy applicator is disabled.

The protected volume (PV), when defined, may be stored by the controller 30. Once anatomical registration is performed with the navigation system 32, the anatomical model (AM) and corresponding protected volume (PV) become linked to the anatomical volume (A). This enables the manipulator controller 60 to control the tool 20 relative to the tracked anatomical volume (A) for avoiding milling in the protected volume (PV).

To implement the protected volume (PV), the software program 80 may utilize the boundary generator 66 to define one or more virtual boundaries 70 for delineating the surfaces between the resection volume (RV) and the protected volume (PV). Alternately, the protected volume (PV) can be defined offline as part of a CAD model for each implant size.

There are various techniques for carrying out the protected volume (PV). Any of these techniques may be utilized as inputs in generating the milling path 100 and/or controls utilized during milling, as described herein.

With reference to FIG. 5, and according to one example, the protected volume (PV) and the resection volume (RV) are at least partially defined using an allowed volume (AV). For the implant-specific virtual boundary case, the allowed volume (AV) can be defined (manually) offline as part of a CAD model for each implant size. The allowed volume (AV) could be input data for the system 10, used by the clinical application 74 and passed into the geometric engine 72 at runtime. Even for an implant-specific allowed volume (AV), the resection volume (RV) could still be patient specific, since the geometric intersection with the patient-specific anatomical model (AM) can be done intra-operatively after implant placement is defined by the surgeon.

The allowed volume (AV) at least partially intersects the anatomical volume (A). The protected volume (PV) may be defined by any volumetric region (or portion thereof) not included within the allowed volume (AV).

The allowed volume (AV) is the region where milling is potentially allowed. The allowed volume (AV) is a subset of (often less than, but at a maximum being equal in volume to) the region where the tool 20 is allowed to move. The allowed volume (AV) is potentially more restrictive than the region where the tool 20 is allowed to move. In order to mill, the tool 20 must be able to move. However, in order to move, the tool 20 does not need to be able to mill. The less restrictive region where the tool 20 is able to move is important to allow the user to move the tool 20 in and out of the resection volume (RV) during the procedure, for example, to get the tool 20 out of the way in order to clean up soft tissue, apply suction, inspect the anatomy, etc.

In some instances, the allowed volume (AV) may be understood as a "keep in" volume, in terms of the milling path generation. The virtual boundaries 70 are often "keep out" boundaries. Any combination of keep-in and/or keep-out virtual boundaries 70 may be mixed along with a keep-in allowed volume (AV) since the allowed volume (AV) part is used for the semi-autonomous or autonomous milling path generation.

After the intersection of allowed volume (AV) with the anatomical model (AM) takes place to compute the resection volume (RV), the sections (S) intersect with the resection volume (RV). The sections (S) may also intersect the allowed volume (AV). The intersection of the section (S) and the allowed volume (AV) is an allowed area (AA).

The allowed volume (AV) comprises the resection volume (RV). The resection volume (RV) can be defined by intersection of the allowed volume (AV) and the anatomical model (AM). The allowed volume (AV) may be customized based on implant model (IM) designed for insertion into the anatomical volume (A). In some examples, each implant model (IM) in the electronic catalog may comprise a corresponding and customized allowed volume (AV). Thus, the allowed volume (AV) contains the implant to be inserted.

The allowed volume (AV) further comprises a tool access volume (TAV), as shown in FIG. 5. The tool access volume (TAV) may be seamlessly integrated with the resection volume (RV) and is configured to guide the tool 20 to the anatomical volume (A). The tool access volume (TAV) may be any suitable geometry, such as an access funnel, cone, bubble, hemi-sphere, prism, or the like. The tool access volume (TAV) entry guides the user into the zone. The tool access volume (TAV) guides the user into the resection volume (RV). This is done because the tool access volume (TAV) and allowed volume (AV) are used in part to define the virtual boundary 70 that the user cannot pass through in manual mode, as they are leading the tool 20 into the resection volume (RV). If the user hits the entry of the tool access volume (TAV), the tool 20 is smoothly deflected off the virtual boundary 70 and the tool 20 is guided towards the resection volume (RV). Once inside the tool access volume (TAV) or allowed volume (AV), the user can start the energy applicator and enable semi-autonomous or autonomous milling.

4. Footprint of Resection Volume

It is important that the resection volume (RV) defines the 'mating surface' (footprint) of the resected anatomy with the implant. The footprint (FP) is a feature of the resection volume (RV). As shown in FIGS. 4-11, the resection volume (RV) comprises a footprint (FP).

In one example, the footprint (FP) is derived from geometric features of the implant model (IM). The footprint (FP) comprises one or more surfaces of the resection volume (RV) that are customized based on the volume of the implant model (IM). In this example, the footprint (FP) may also be understood as the contact surface(s) of the implant with the resected anatomical volume (A). The footprint (FP) may be a lower, upper, or side contact surface. The footprint (FP) may be planar or non-planar and may take any primitive or complex shape depending on the simplicity of the planned resection volume (RV) or implant model (IM).

The path 100 does not need to align with the footprint (FP). The path 100 could be spaced deeper to allow room for the use of an adhesive like bone cement, or could be higher to allow for a press fit of the implant.

The alignment to the footprint (FP) can be variable around the perimeter of the path 100. An operator may want to have press fit areas and not a press fit on the entire implant edge. This could be user selected as an input to the cutting volume.

In configurations where the implant model (IM) includes a corresponding allowed volume (AV), the footprint (FP) may be understood as the common (intersecting) surface(s) of the implant model (IM) and allowed volume (AV).

The geometric engine 72 may comprise an algorithm for defining the footprint (FP). The algorithm may generate the footprint (FP) using interpolation, least squares approximation, and/or shape approximations derived from the geometry of the implant model (IM). Hence, the footprint (FP) may be freeform surface or a CAD modeled surface.

Techniques have been described above for generating the resection volume (RV) without the implant model (IM). Hence, defining the footprint (FP) without the implant model (IM) is possible. For example, the resection volume (RV) may be defined from the portion of the anatomical model (AM) that is above the planar surface of the protected volume (PV). In such instances, the footprint (FP) is planar and defined by the protected volume (PV) rather than the implant model (IM).

The footprint (FP) can be identified by the software program 80 for purposes of planning the milling path 100 according to the techniques described herein.

5. Offset Boundary for Resection Volume

As described, the tool 20 is tracked relative to the anatomical volume (A). After registration, interaction between the tool 20 and the resection volume (RV) can be monitored or visualized simultaneously as the tool 20 mills the anatomical volume (A). In one example, the TCP of the tool 20 that is tracked is the spherical center of the burr 25.

Figure 7:
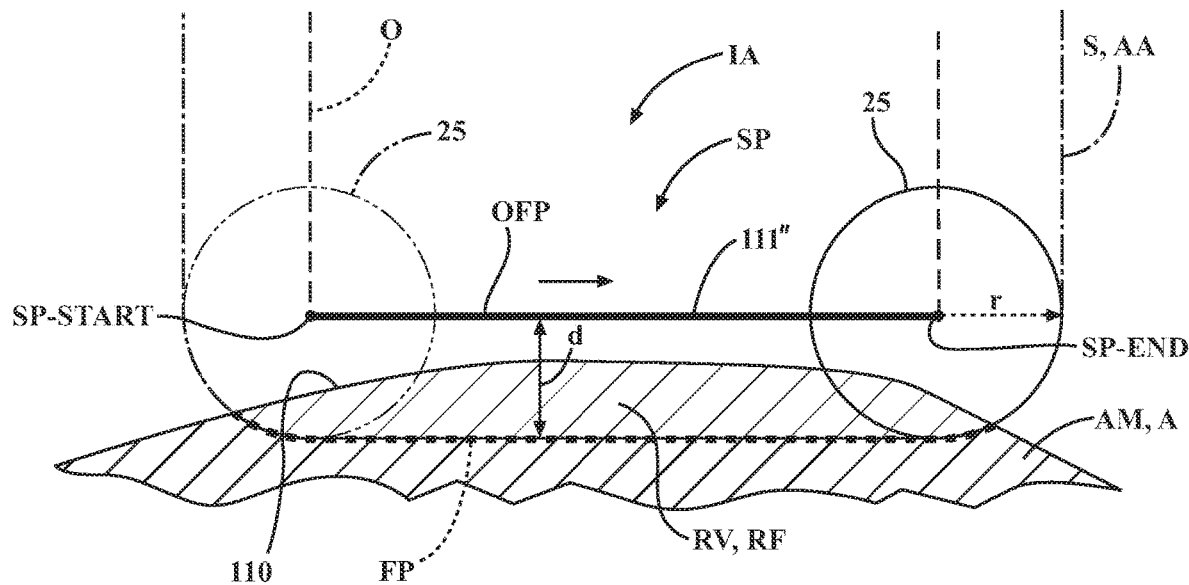
FIG. 7 is one example of the section path defined for milling the resection face having a plateau, as shown.

As shown in FIG. 7, the spherical burr 25 comprises radius (r) defined from the TCP. As the TCP is tracked relative to the resection volume (RV) for milling, the radius (r) of the burr 25 should be accounted for when generating the milling path 100. Mainly, the exterior surface of the burr 25 engages the anatomical volume (A), not the virtual TCP. Therefore, generating the milling path 100 without accounting for the burr 25 radius (r) may result in the burr 25 milling beyond the resection volume (RV), e.g., by a distance equivalent to the radius (r). The same technique may apply for the use of a saw. Here, the swing range of the saw blade can be substituted for (r). When using a tapered burr or a contoured cutter there could be an (r) value that varies based upon the depth of the cut.

Accordingly, the software program 80, with the assistance of the geometric engine 72 and boundary generator 66, is configured to generate an offset boundary (O), as shown in FIGS. 5 and 7-11. In one example, the offset boundary (O) is to account for the geometric characteristics of the tool 20. Alternatively, the offset boundary (O) may be to facilitate modifying the resection volume (RV) for patient specific parameters. Hence, the offset boundary (O) may correspond to a patient specific parameter.

The offset boundary (O) is a virtual planar or non-planar boundary 70. In one example, the offset boundary (O) is configured to direct collision detection, such as 'point to mesh' collision detection. Here, the milling path 100 may be computed with the offset boundary (O), since the offset boundary (O) may give the desired path of the TCP.

The offset boundary (O) is defined relative to the resection volume (RV). The offset boundary (O) may be defined within or beyond the resection volume (RV). Where there is the allowed volume (AV), the offset boundary (O) may be defined within the allowed volume (AV). The offset boundary (O) may extend beyond the resection volume (RV) in a direction extending away from the bone/tissue being milled, in order to protect soft tissue or to avoid other objects.

The intersection of the offset boundary (O) and the allowed volume (AV) is an inner volume (IV), as shown in FIG. 5. The intersection of the section (S) and the offset boundary (O) is an inner area (IA), as shown in FIGS. 7-11. The inner area (IA) excludes the area spaced between the footprint (FP) and the offset boundary (O). The inner area (IA) may or may not intersect the resection volume (RV).

The offset boundary (O) is spaced apart from one or more surfaces the resection volume (RV). Such surfaces may be the footprint (FP) of the resection volume (RV), as shown in FIG. 5. In such examples, the offset boundary (O) may be understood as an offset footprint (OFP).

The offset boundary (O) is spaced apart by an offset distance (d), as shown in FIGS. 5 and 7. In the example described, the offset distance (d) is the radius (r) of the burr 25. Of course, the offset distance (d) may be different depending on the geometric characteristics of the tool 20 and corresponding TCP defined for the tool 20. The offset distance (d) may be constant or variable throughout the length of the offset boundary (O). The surface of the offset boundary (O) may be planar or curved. The offset distance (d) may also be defined based on factors unrelated to geometric features of the tool 20. As described below, the user may select an offset distance (d) using the software program 80.

The offset boundary (O) may or may not be utilized in planning and generating of the milling path 100. When utilized, the offset boundary (O) may have configurations or features other than those described specifically herein.

C. Reference Guide

Figure 4:
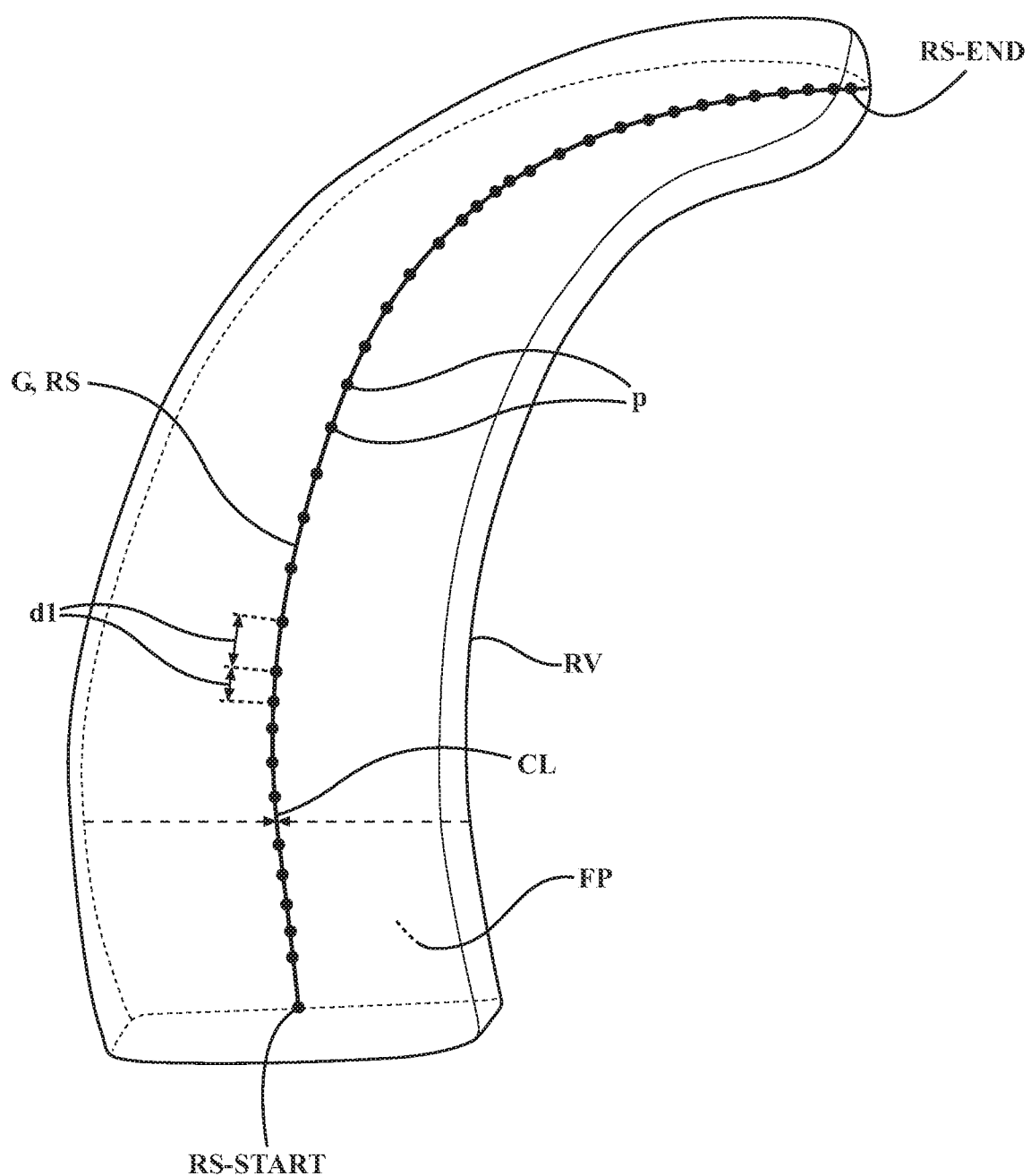
FIG. 4 is a sample illustration of the resection volume having a virtual reference guide (e.g., a reference spline) defined relative thereto in furtherance of generating the milling path.
Figure 6:
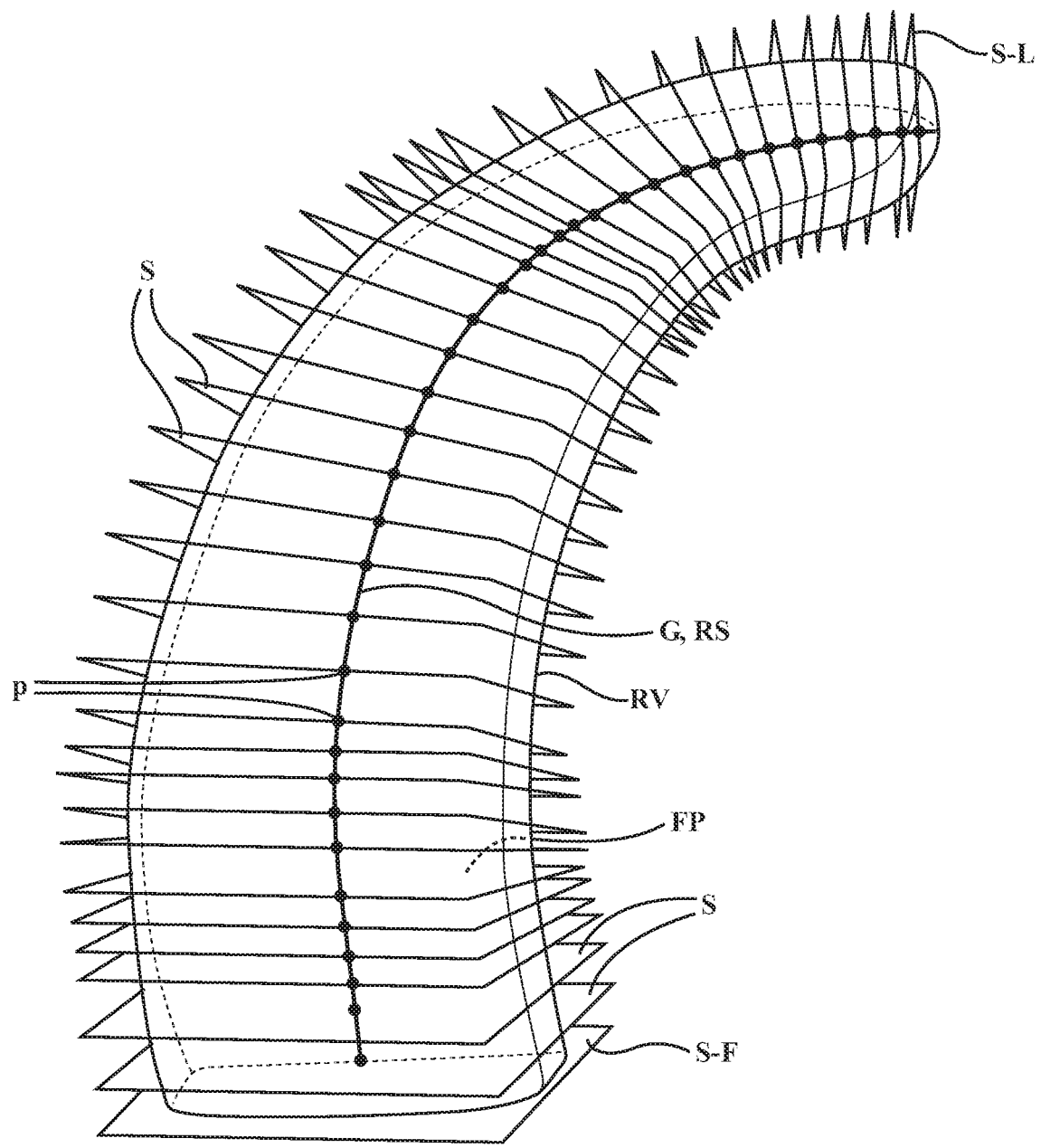
FIG. 6 is the resection volume of FIG. 4 having sections defined successively along the reference spline for orienting numerous section paths for the milling path.

With the resection volume (RV) defined, the milling path 100 can be planned for removing the same. To do so, the planned milling path 100 is guided with respect to geometry of the resection volume (RV). The software program 80, with the assistance of the geometric engine 72, is configured to define a reference guide (G), as shown in FIGS. 4-6. The reference guide (G) is a feature derived from the geometry of the resection volume (RV). As will be understood below, the reference guide (G) is used to define positioning of various segments of the milling path 100. The reference guide (G) may be a freeform CAD modeled geometry.

The software program 80 is configured to evaluate the geometry of the resection volume (RV) and to automatically generate the reference guide (G) based on the outcome of the evaluation. For example, the geometric engine 72 may comprise an algorithm for defining the reference guide (G). The algorithm may generate the reference guide (G) using interpolation, least squares approximation, and/or shape approximations derived from the geometry of the resection volume (RV).

The reference guide (G) may or may not be visualized by the user. The reference guide (G) can be drawn, modeled, or adjusted by the surgeon using the input devices 40, 42 of the navigation system 32.

When generated, the reference guide (G) can be associated with geometry of the resection volume (RV) in numerous ways. For example, the reference guide (G) may be associated with landmark points, lines, surfaces/planes, vertices, or any volumetric portion of the resection volume (RV). In one example, the reference guide (G) is defined with respect to the footprint (FP) of the resection volume (RV). This way, the reference guide (G) is designed to guide milling with a particular focus on geometric features of the implant model (IM). For example, the reference guide (G) may follow the centerline of the implant footprint. Also, rather than being computed on-the-fly, the reference guide (G) may be included in a CAD model along with the implant model (IM) and allowed volume (AV) as part of an electronic catalog or implant database.

The techniques described herein may be utilized to generate reference guides (G) having various configurations that are derived from the geometry of the resection volume (RV). Such reference guides (G) may include one or more of guide points, guide lines, guide surfaces, guide volumes, or any combination thereof.

1. Reference Spline

One example of the reference guide (G) is a reference spline (RS) shown in FIGS. 4-6, which is explained further below. Any description herein relating to the reference spline (RS) may be substituted with alternative configurations for the reference guide (G).

The reference spline (RS) is a virtual 3D curve or spline that is derived from or based on geometry of the resection volume (RV). The reference spline (RS) may be a freeform curve, CAD modeled curve, and/or a sequence of points.

The software program 80 can define the start and end points (RS-START, RS-END), as shown in FIG. 4, as well as the curve of the reference spline (RS). These points can be defined automatically or alternately these points may be defined manually offline, and imported along with the implant and allowed volume (CAD) models. Additionally or alternatively, the reference spline (RS) may be directly created based on user selective manipulation of the start and end points (RS-START, RS-END) and path of the reference spline (RS). The orientation of RS-START, RS-END can be different from that shown in the drawings and may be chosen as best suited for the milling plan.

In one example, as shown in FIG. 4, the reference spline (RS) is defined more specifically with respect to the footprint (FP) of the respective volume (RV). One technique for implementing this association is by the geometric engine 72 approximating a center line (CL) of the footprint (FP). The center line (CL) is a characteristic of the footprint (FP) geometry. In an oversimplified example, if the footprint (FP) is a rectangular plane, the center line (CL) is a line of symmetry of the rectangle. However, the footprint (FP) is more likely to be a contoured surface. In such scenarios, the geometric engine 72 can compute the center line (CL) of the footprint (FP) using any suitable algorithm. In one example, the center line (CL) is determined by defining a contoured perimeter of the footprint (FP), computing successive contoured lines connecting opposing sides of the contoured perimeter, and by identifying a mid-point of each contoured line. The mid-points can then be connected to define the contoured reference spline (RS). Such computations can be an approximation and need not be exact directly opposing sides or mid-points. As will be understood below, the sections (S) provide geometric tolerance to account for such approximations of the reference spline (RS).

With the center line (CL) computed, the reference spline (RS) can be associated therewith. In FIG. 4, the geometric engine 72 may align the reference spline (RS) to the center line (CL). Alignment between the reference spline (RS) to the center line (CL) may be partial or an entire. Alternatively, alignment could be done manually along the center line (CL) as part of an imported model based on the implant and allowed volume (AV) geometry.

Figure 6A:
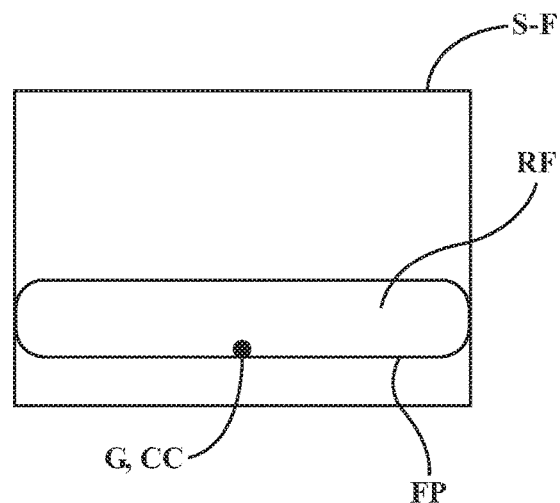
FIG. 6A is a front view of the first section of FIG. 6, showing a resection face of the resection volume intersected by the first section.
Figure 6B:
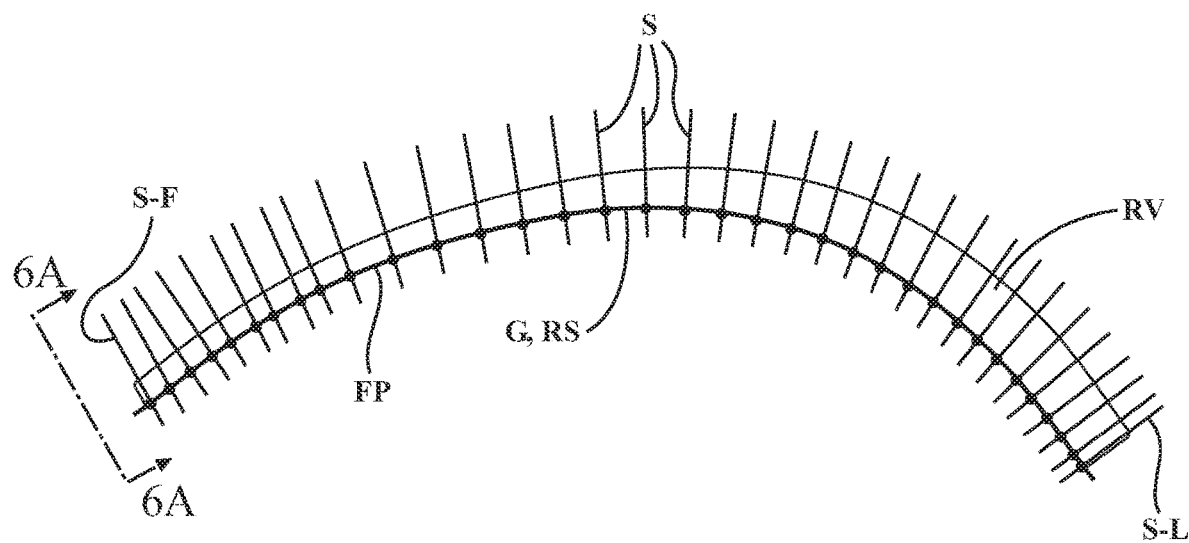
FIG. 6B is a side view of the resection volume, reference spline, and sections of FIG. 6.

Additionally or alternatively, the reference spline (RS) may further be coincident with the footprint (FP). In other words, the reference spline (RS) can be understood as lying directly on or in the footprint (FP), as shown in FIGS. 4 and 6A-6B. Alternatively, the reference spline (RS) can be aligned with the center line (CL) yet non-coincident with the footprint (FP). In other words, the reference spline (RS) may be offset above or below the footprint (FP). For example, as shown in FIG. 5, the reference spline (RS) is directly on the offset boundary (O) and offset footprint OFP, rather than on the footprint (FP) itself.

Defined by the center line (CL) technique or otherwise, the reference spline (RS) may exhibit various characteristics. For example, the reference spline (RS) may be disposed entirely or partially within the resection volume (RV). Alternatively, the reference spline (RS) may be disposed completely outside of the respective volume (RV). The reference spline (RS) may be disposed along one or more surfaces of the resection volume (RV). The reference spline (RS) may be surrounded by the space of within resection volume (RV) without intersecting any surfaces of the resection volume (RV). Alternatively, the reference spline (RS) may intersect any surface of the resection volume (RV).

The reference spline (RS) start and end points (RS-START, RS-END) may terminate within the resection volume (RV), at a perimeter surface of the resection volume (RV), or at a point beyond the perimeter surface of the resection volume (RV). When aligned to the center line (CL), the start and end points (RS-START, RS-END) of the reference spline (RS) may align to end points of the center line (CL).

Path 100 could be completed in multiple pieces. For a complex shape, it may be desirable to divide the resection volume (RV) into sub-volumes, create the path 100 for each sub-volume, and then re-combine paths to create the full path.

Depending on the complexity of the resection volume (RV), the reference spline (RS) may be complex or simple. The reference spline (RS) may have segments that are linear, curvilinear, curved, arced, sloped, tangential, piecewise, zig-zag, spiral, wavy, or the like. Furthermore, the reference spline (RS) may be a continuous curve or may comprise one or more smooth curve segments. Furthermore, the reference spline (RS) may be a line or contained within a guide strip. Examples and characteristics of the reference spline (RS) other than those described herein are fully contemplated.

D. Sections

With the reference spline (RS) defined with respect to the resection volume (RV), the software program 80 can execute next steps for planning and generating the milling path 100. With the assistance of the geometric engine 72, the software program 80 intersects the resection volume (RV) into discrete cut sections (e.g., planar or non-planar surfaces).

Mainly, the software program 80 computes a plurality of sections (S), as shown in FIGS. 3, 5, 6-11. The sections (S) are defined along the reference spline (RS). The sections (S) may be planar or non-planar. In one example, the sections (S) are section planes. The sections (S) are defined in succession along the reference spline (RS). In another example, the sections (S) may be a sequence of non-planar (e.g., curved) sections that each get flattened out temporarily for creating the section tool path, and then projected back on to their respective curved sections before the transition segments are created. Other techniques for generating the sections (S) are possible as well. The reference spline (RS) helps to define or position the sections (S), and hence, the corresponding section path (SP), as will be described below. Using sections (S) enables high-quality preparation of the milling path 100, particularly when the milling path 100 is prepared on-the-fly and for freeform implants.

1. Section Sizing and Spacing

Each section (S) intersects the reference spline (RS) (or vice-versa) at a different intersection point (p), as shown in FIGS. 4-6. The sections (s) may be finite or infinite sections (S). The intersection point (p) is primarily for orienting the section (S) relative to the reference guide (G) and can be located anywhere on the section (S). For example, the intersection point (p) can be defined anywhere with respect to the surface area or perimeter edges of the section (S), or defined at a center point or origin of the section (S). Alternatively, the intersection point (p) can be an offset (non-centered) point or a point on the perimeter edge of the section (S).

The software program 80 may define one or more sections (S) along the reference spline (RS). In one example, the software program 80 designates at least a first section (S-F) and a last section (S-L), as shown best in FIGS. 6, 6A and 6B. The first plane (S-F) designates the first slice of the resection volume (RV) that the tool 20 should mill. The last section (S-L) designates the last slice of the resection volume (RV) that the tool 20 should mill. Optionally, any number of sections (S) may be defined between the first section (S-F) and last section (S-L). In another example, the resection volume (RV) may be small enough relative to the tool 20 radius that only one section (S) could be generated.

The intersection points (p) are spaced apart from one another along the reference spline (RS) by a distance (d1), as shown best in FIG. 4. The distance (d1) between any number of intersection points (p) may be constant or equidistant, or evenly distributed. Alternatively or additionally, as shown in FIG. 4, the distance (d1) between any number of successive intersection points (p) may be variable or non-equidistant. The intersection points (p) in FIG. 4 are shown for reference and clarity in illustration in view of the fact that sections (S) are not shown in FIG. 4.

The software program 80 may consider several factors in determining the distance (d1) between the intersection points (p). These factors may be derived from data obtained from sensors, from user input, and/or derived by the controller 30 using any suitable source or technique. Any of the factors below may be utilized individually or in combination.

One factor is characterization of cutting performance of the tool 20 under nominal or worst-case conditions, which can be determined offline. Using milling terminology, the section (S) spacing can be considered the 'depth of cut', which is often less or much less than the burr radius (r). This setting may be chosen based on trade-off between milling accuracy and milling time requirements.

Another such factor is geometric characteristics of the tool 20, e.g., the radius (r) of the burr 25. The distance (d1) may be set to the radius (r) so that there is some overlap in milling. This setting may be a 'worst-case' setting, representing the most aggressive cut. The distance (d1) is more likely to be set at less than the burr radius (r). Other parameters of the tool 20 may be considered, such as mechanical tolerances, sensitivity, flexibility, and/or material composition of the burr 25 and/or bone/tissue. Greater distance (d1) may be desirable to avoid exceeding limitations of the tool 20, particularly in view of parameters of the anatomical volume (A). Lesser values of (d1) increase cutting accurate and greater values of (d1) increase milling efficiency. In one example, the parameter is (bone or tissue) mineral density, e.g., analyzed from the pre-operative imaging. Another parameter may be tissue impedance. Quantification of such factors may be derived from imaging of the anatomical volume (A), sensing forces and/or torques applied to the tool 20, or the like. The software program 80 can consider these characteristics to appropriately define the distances (d1) to avoid damaging the tool 20 and/or the anatomical volume (A). Forces/torques can be measured by the force/torque sensor on the manipulator 14, motor torque (i.e., motor current) applied by the tool 20, joint torque sensors in the manipulator 14, joint motor torque (i.e., motor current) applied by the manipulator 14, etc. For these cases, the upcoming section (S) could be computed on-the-fly, based on the force/torque measurements derived from milling of earlier sections (S). If the force/torque is high, the distance (d1) could be reduced for upcoming sections (S), and vice versa.

Heating of the anatomy may be another factor. The path 100 may need to be adjusted as a result irrigation provided by the system. Alternatively, the feed rate may be maintained, but the volume of irrigation may increase. With this integrated technique, the planned feed rate may be decreased if the algorithm is able to dynamically adjust the milling parameters because a surgeon prefers manual irrigation, etc.

Another factor may be the geometry of the resection volume (RV). For simpler geometries of the resection volumes (RV) (e.g., planar surfaces), equal spacing of the intersection points (p) may be more appropriate. On the other hand, where the geometry of the resection volume (RV) is more complex (e.g., contoured), variable spacing may be more suitable. This factor affects aggressiveness of the handling of the tool 20 and potentially the milling depth. For contoured paths, the distance (d1) could be measured 'along the path' (i.e., path length).

The software program 80 may also take into account a desired surface finish for the resected surface of the anatomical volume (A). As the distance (d1) decreases, the accuracy, and smoothness of the milling increases. Conversely, as the distance (d1) increases, the accuracy and smoothness of the milling decreases.

Another consideration relates to milling time. Increased/decreased milling time is based on the increase/decrease in path length, respectively. By adjusting the distance (d1) to be smaller, milling is more accurate but results in a longer path length. By adjusting the distance (d1) to be greater, milling is less accurate but results in a shorter path length. Hence, there is a tradeoff between milling accuracy and milling time. In one example, the software program 80 balances this trade off by computing the shortest path length subject to a defined 'acceptable' accuracy. From this analysis, the software program 80 can select the largest value of (d1) that meets the accuracy requirement. This tradeoff in choosing (d1) is valid whether the sections (S) and tool path are generated on-the-fly, or not (i.e., before or after implant placement is defined or adjusted, and before or while milling).

Other factors considered in calculating the distance (d1) may be anatomical properties. Anatomical properties may include bone density. Voxel brightness can be sampled (e.g., potentially computing bone density from CT brightness) along the reference spline (RS) and the distance (d1) can be set greater for lower density and lesser for higher density. Alternatively, a sample spacing (e.g. equal to start) could be used, then the average voxel brightness (or average density in the section (S)) can be computed. The sections (S) can then be subdivided for dense regions or decimated (removed) for less dense regions. A mathematical function may be utilized to derive a new spacing based on the sample spacing/brightness calculation. Optimized spacing (d1) can be iteratively determined based on the brightness/density.

Factors other than those describe above may be considered by the software program 80 when calculating the distance (d1) between any number of successive intersection points (p). Moreover, the factors described above may be utilized in computing any other feature of the milling path 100 described herein.

Each section (S) is designed to intersect the resection volume (RV), or vice-versa. The sections (S) are representative of the resection volume (RV) because the sections (S) are defined with respect to the underlying reference spline (RS) derived from of some geometry (e.g., such as the center line CL) of the resection volume (RV).

As described, the sections (S) can be infinite and the size of each section (S) is of less importance because only the part of the sections (S) that intersects the resection volume (RV) will be machined. Hence, the area/perimeter edges of the section (S) may be defined by the geometric engine 72 to encompass or extend beyond a cross-sectional area of the resection volume (RV) intersected by the section (S).

The geometric engine 72 calculates the intersection of the section (S) with the resection volume (RV). This intersection (which may be an area or a volume) is called a resection face (RF), and will be described below.

Any one or more of the sections (S) can also be designed to intersect the offset boundary (O) where utilized, or vice-versa. The sections (S) can also intersect virtual geometries other than those described herein.

The sections (S) can be any surface or shape, including any number of sides, vertices, and with any suitable area. Any of the sections (S) may have the same or different shape or area, depending on factors such as the corresponding cross-sectional area of the resection volume (RV) and/or location of the offset boundary (O) relative to the respective section (S).

2. Section Orientation

The software program 80, with the assistance of the geometric engine 72, is configured to define each section (S) at a specified orientation relative to the reference spline (RS) at the intersection point (p).

The orientation of the section (S) can be defined relative to the intersection point (p) of the section (S). The section (S) orientation can be tilted, rotated, turned, or otherwise manipulated while maintaining the position of the origin relative to the surface area of the section (S). The section (S) can be oriented relative to the reference spline (RS) (or intersection point (p)) according to any angle relative to any axis.

In simpler cases, two or more sections (S) may be at the same orientation relative to the reference spline (RS). Alternatively, two or more sections (S) may be at a different orientation relative to the reference spline (RS).

Orientation of the section (S) has an impact on the orientation of the milling path 100, and more specifically, the orientation of the section path (SP) defined with respect to corresponding section (S), as will be described below.

In one technique, the software program 80 defines the orientation of the section (S) to optimize intersection of the section (S) with the resection volume (RV). For example, for any given intersection point (p), the geometric engine 72 can sweep the section (S) through a range of orientations. The geometric engine 72 can evaluate the surface area intersection between the section (S) and the resection volume (RV) throughout the range. The geometric engine 72 can then fix the section (S) relative to the reference spline (RS) at the orientation causing the greatest surface area intersection between the section (S) and the resection volume (RV). The geometric engine 72 can use other techniques for selecting the orientation.

The software program 80 may specify orthogonal orientation of the sections (S) for other reasons, such as for reducing milling error relative to the anatomical volume (A), and more specifically, relative to the footprint (FP). Here, the geometric engine 72 defines the orientation of the section (S) to be orthogonal to the reference spline (RS) at the intersection point (p). In other words, the sections (S) collectively are disposed in an orthogonal trajectory wherein each section (S) intersects the reference spline (RS) at a right angle. The reference spline's (RS) tangent at point (p) would be the normal vector of the section (S). The section (S) can be defined by its normal vector (i.e., the tangent of the reference spline (RS) at point (p) for this example) and a point on the section (S), i.e., point (p).

The orthogonal relationship between the sections (S) and reference spline (RS) does not require successive sections (S) to be parallel to one another. As described, the reference spline (RS) is a curve and, depending on the complexity of the footprint (FP) for example, may have aggressive contours as compared with a flat surface. Therefore, successive sections (S) oriented orthogonal to the reference spline (RS) are likely to be oriented transverse relative to one another. On the other hand, if the reference spline (RS) were a straight (non-contoured) line, the successive sections (S) oriented orthogonal to the reference spline (RS) are likely to be oriented parallel relative to one another.

E. Section Path

The software program 80, with the assistance of the geometric engine 72 and the path generator 68, is configured to generate portions of the milling path 100 for each section (S). These portions are the aforementioned section paths (SP) and are shown throughout FIGS. 7-15. The section paths (SP) are parts of the milling path 100 where the majority of milling is performed. The section paths (SP) will be combined with other portions to generate the entire milling path 100.

1. Design Overview

To reiterate, each section path (SP) is defined with respect to a corresponding section (S). More specifically, the geometric engine 72 computes the intersection of the section (S) with the resection volume (RV). This intersection is the resection face (RF), which is the slice of the resection volume (RV) intended for milling. The resection face (RF) can be a planar or non-planar geometrical object. The resection face (RF) is a bounded subset of the section (S). Examples of the resection faces (RF) are shown in FIGS. 6A and 7-11.

The section path (SP) is designed to remove the resection face (RF). The remaining area of the section (S) that does not include the resection face (RF) is either a prohibited region or unoccupied by anatomy.

The section paths (SP) can be planar or non-planar. The section paths (SP) may be complex surfaces. The surface shape could propagate through the volume with similar spacing. An example would be mapping the section paths (SP) on a bowl shape, then stacking the bowl shapes to generate the complete path. The resection volume (RV) can be intersected by geometries patterned along the reference spline (RS) to generate segments.

The section path (SP) can be bounded within the resection face (RF). Alternatively, the section path (SP) can be partially or entirely beyond the resection face (RF). Non-overlapping between the section path (SP) and the resection face (RF) can still provide milling because the radius (r) of the burr 25 extends into the resection face (RF). Examples of this will be described below.

Positioning of the section paths (SP) with respect to the resection volume (RV) is based on the reference spline (RS), or more specifically, based on the respective point (p) on the reference spline (RS). Orientation of the section paths (SP) is based on the orientation of the respective section (S).

Orientation of the section path (SP) can have an impact on the positioning of the TCP during milling. The TCP is monitored by the controller 30 during milling of the section path (SP) for removing the anatomical volume (A) along the specified orientation. Orientation of the section path (SP), may also affect the desired orientation of the tool 20. The controller may use the section path (SP) angle to determine orientation for the tool 20, or could decide/control the orientation of the tool 20 through independent means, e.g., through user input, applied forces/torques, etc.

In some instances, the controller 30 may restrict orientation of the tool 20 such that the burr 25 engages the section path (SP) in a specified angle relative to the section (S). Other orientations of the tool 20 are fully contemplated.

When the successive section paths (SP) are oriented orthogonal to the reference spline (RS), milling error relative to the anatomical volume (A) (and the footprint FP) is reduced compared with section paths (SP) oriented non-orthogonal to the reference spline (RS). Mathematically, milling along successive section paths (SP) that are orthogonal to the reference spline (RS) produces greater overlapping milling coverage as compared with milling along successive section paths (SP) that are not orthogonal to the reference spline (RS). In turn, the orthogonal section paths (SP) cause smoother surface approximations for the anatomical volume (A) and footprint (FP) for given distance(s) (d1).

The section path (SP) can be designed and the controller 30 can be configured to control motion of the tool 20 to maintain the tool 20 a certain depth relative to the section path (SP). The design consideration here is to address how far into the section path (SP), or section (S), the tool 20 penetrates during milling. Where the burr 25 is spherical, the spherical center (TCP) may be the point controlled/tracked to traverse along the section path (SP). The amount of material that is removed depends on the spacing of the preceding section (S). Some of the material may already have been removed from the prior section path (SP) if the preceding sections (S) were spaced closer together than the burr radius (r). This spacing should extend beyond the resection volume (RV), such that the first section (S-F) only partially interacts with the bone/tissue. This is a consideration that may be taken into account when designing the reference spline (RS) and location of its first point (RS-Start). The amount of material removal (i.e., depth of cut) per each section path (SP) can be configured by setting the distance(s) d1 between sections (S).

The depth of penetration into the section path (SP) may be set in various ways. In one example, the origin of the TCP follows the section path (SP) directly. Alternatively, the origin of the TCP may be offset from the section path (SP) by any suitable distance. The offset may be different from section (S) to section (S). For instance, the offset for the TCP at the first section (S-F) may be different from another section (S).

Just as with the sections (S), the software program 80 may define one or more section paths (SP) along the reference spline (RS). For a very thin resection volume (RV), e.g., less than the burr radius (r), it is feasible to have solely one section path (SP).

Figure 15:
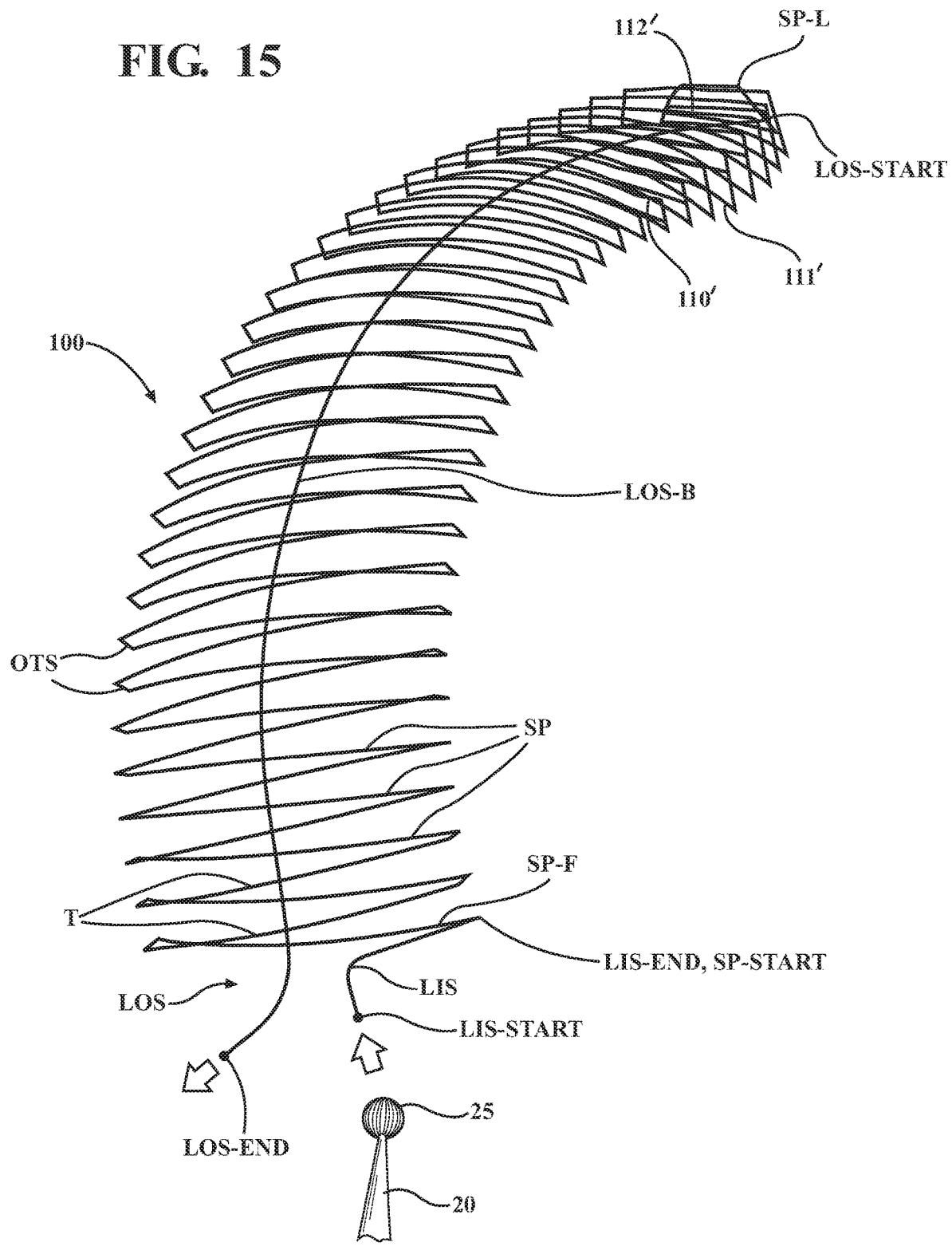
FIG. 15 is one example the milling path designed according to the techniques described herein, for removing the resection volume of FIG. 4.

The software program 80 designates at least a first section path (SP-F) as shown in FIG. 15, and optionally a last section path (SP-L). The first section path (SP-F) is the first section path that the tool 20 traverses along the milling path 100. The last section path (SP-L) is the last section path that the tool 20 traverses along the milling path 100. Depending on the number of sections (S), any number of section paths (SP) may be defined between the first section path (SP-F) and last section path (SP-L).

As an additional optimization, the software 80 could evaluate whether the last section path (SP-L) was needed, or if the material would already have been fully removed from the preceding section path (i.e., SP-F for this case).

Figure 9:
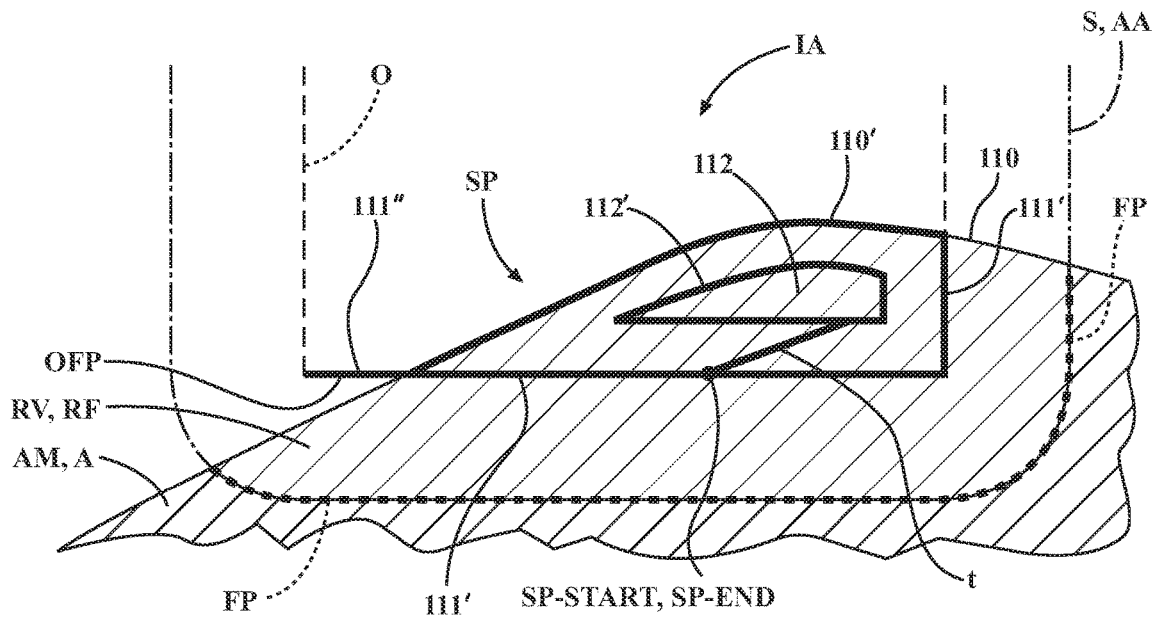
FIG. 9 is one example of the section path defined for milling the resection face having a slope, as shown.
Figure 12:
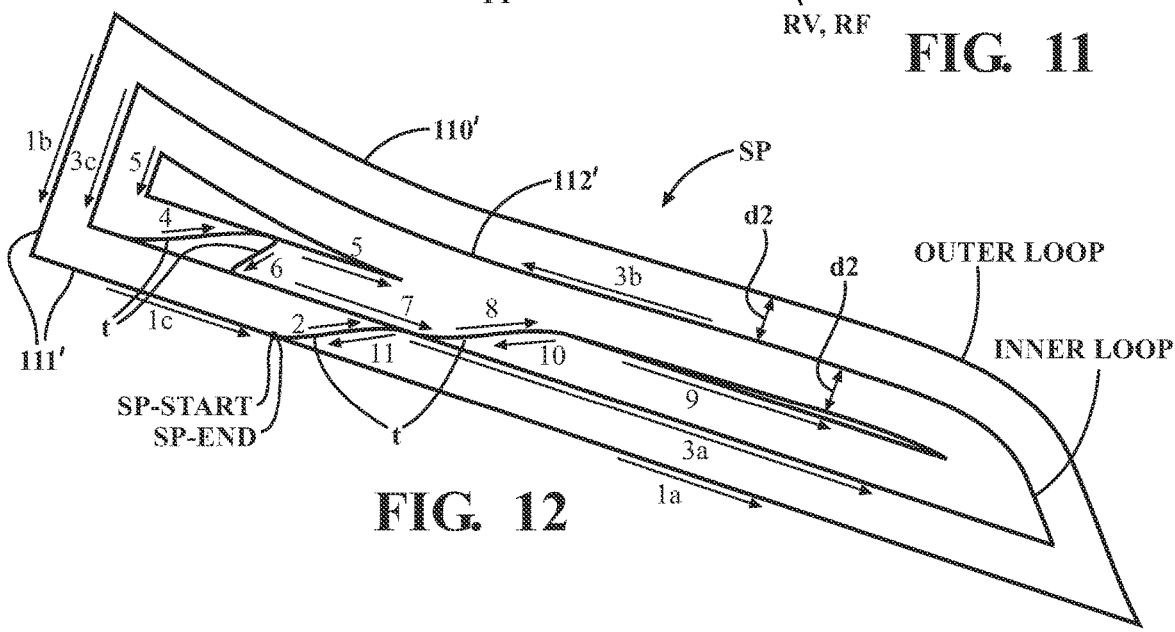
FIG. 12 is one example of a more complex section path with reference to segments traversed, in order, by the tool throughout the section path.

Each section path (SP) has a starting point (SP-START) and an ending point (SP-END), as shown in FIGS. 7, 9 and 12, for example. The starting point (SP-START) and ending point (SP-END) are located on the section (S) and can be chosen based on default positions or positions for optimizing the tool path. In one example, as shown in FIG. 9, the starting point (SP-START) and ending point (SP-END) are each bounded within the resection face (RF). Alternatively, as shown in FIG. 7, the starting point (SP-START) and/or ending point (SP-END) can be outside of the resection face (RF). Milling for the section path (SP) begins at the starting point (SP-START) and finishes at the ending point (SP-END). The starting point (SP-START) and the ending point (SP-END) can sometimes be the same point, as in FIGS. 9 and 12. As will be described below, techniques are provided for transitioning between section paths (SP), or more specifically, from the ending point (SP-END) of one section path (SP) to the starting point (SP-START) of another section path (SP). With the single-pass milling techniques provided herein, milling continues along the entire path of each section path (SP), i.e., from the starting point (SP-START) to the ending point (SP-END).

As described above, the section path (SP) is designed to remove the resection face (RF), i.e., the slice of the resection volume (RV) intersected by the section (S). Resection volumes (RV) are likely to have different geometric features along the reference spline (RS), such as edges, contours, valleys, hills, as well as variable dimensions (e.g., width, height). Hence, any given cross-section of the resection volume (RV) along the reference spline (RS) is likely to produce various shaped resection faces (RF). Accordingly, the software program 80 generates customized section paths (SP) that are uniquely tailored to remove such various resection faces (RF).

The section path (SP) can be an open path (e.g., open-ended), as shown in FIG. 7, for example. In another example, as shown in FIGS. 8-12, the section path (SP) is a closed path (e.g., ends touching). Examples of such section path (SP) are described below.

i. Perimeter Segments

Referring to FIGS. 7-11, the resection face (RF) may comprise one or more perimeter edges 110. The perimeter edge 110 may partially or entirely be the cross-sectional perimeter of the resection volume (RV) that intersects the section (S).

Figure 8:
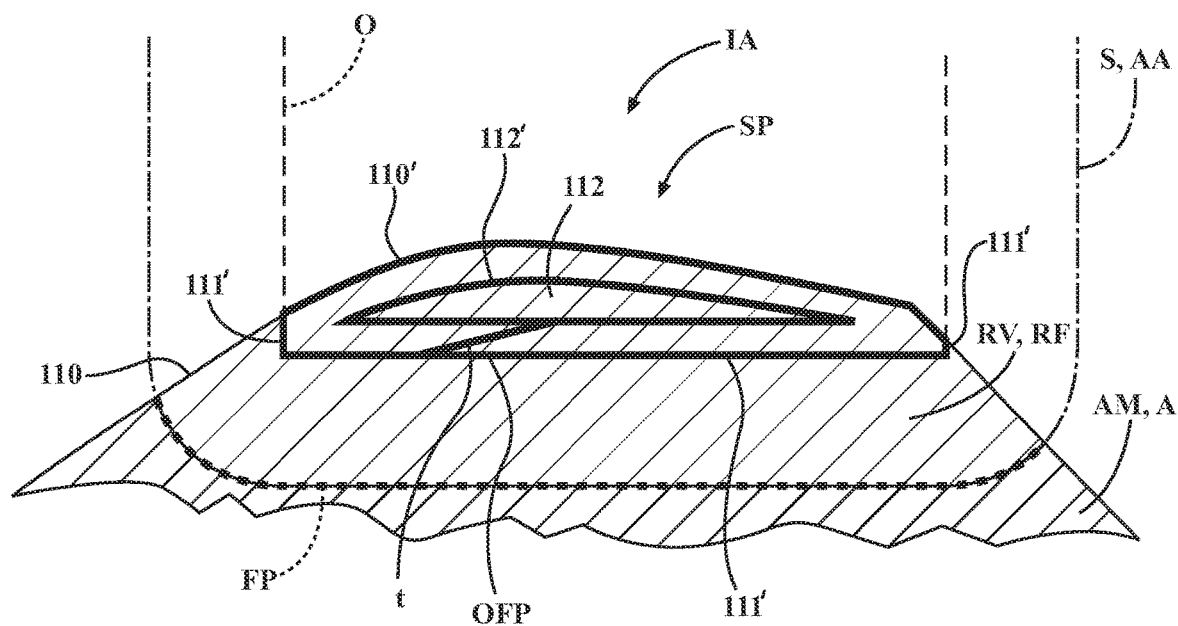
FIG. 8 is one example of the section path defined for milling the resection face having a peak, as shown.

The section path (SP) may be generated with at least one perimeter segment 110'. The perimeter segment 110' is designed to coincide, partially or entirely, with the perimeter edge 110 of the resection face (RF), where present. In FIG. 8, there is one perimeter segment 110'. In FIG. 7, there are no perimeter segments 110'.

The perimeter segment 110' may be linear, contoured, curvilinear, or the like. The perimeter segment 110' may comprise any number of segments, edges, or sides. The resection face (RF) may comprise any number of separate perimeter segments 110'.

ii. Boundary Segments

As described in the examples above, the section path (SP) can be defined at least partly with respect to the perimeter edge 110 of the resection face (RF). However, the section path (SP) additionally or alternatively may be defined with respect to the offset boundary (O). For example, for the spherical burr 25, the offset boundary (O) is utilized to account for the radius (r) of the burr 25.

The section path (SP) can coincide, entirely or partially, with the offset boundary (O). In such instances, the section path (SP) can be said to comprise a boundary segment 111'. Also described below is a floating boundary segment 111", i.e., a type of boundary segment 111'.

In some instances, the offset boundary (O) overlaps the resection face (RF). Hence, the boundary segment 111' coinciding with this type of offset boundary (O) similarly overlaps the resection face (RF), as shown in FIGS. 8-11.

Alternatively, the offset boundary (O) does not overlap the resection face (RF). Hence, the boundary segment 111" coinciding with this type of offset boundary (O) similarly does not overlap the resection face (RF). Such a boundary segment 111" is "floating" because it is separated from the resection face (RF), as shown in FIG. 7 and partially in FIG. 10. An example of this is described below.

Of course, there may be instances where one or more boundary segments 111' partly overlap the resection face (RF) and partly do not overlap the resection face (RF).

The boundary segments 111' may entirely or partially overlap with the offset footprint (OFP) for example.

In one example, the software 80 is configured to evaluate the remaining material after the boundary segment 111' is computed, and only adds a perimeter segment 110' if needed.

iii. Interior Segments

The surface area of the resection face (RF) bounded within the perimeter edge 110 may be entirely milled because of milling around along the perimeter segment 110' and/or the boundary segment 111'. However, in some instances, perimeter and/or boundary milling may not reach certain portions or "islands" of the resection face (RF). In these situations, the software program 80 is configured to identify interior portions 112 of the resection face (RF) that the tool 20 will not reach from perimeter and/or boundary milling, as shown in FIGS. 8, 9 and 12.

With reference to FIGS. 8, 9, and 12, the software program 80 generates one or more interior segments 112' designed to remove the interior portion 112. The interior segments 112' can be designed by the geometric engine 72 using any suitable algorithm or technique.

For example, in one technique, the interior path segment 112' is generated by computing a predetermined distance from the perimeter segment 110' and/or boundary segment 111' in a direction towards the interior portion 112. This distance is an offset (d2), as shown in FIG. 12. The offset (d2) can be manually entered into the system 10. Alternatively, the software program 80 can automatically determine the offset (d2). In one example, the offset (d2) is set to be less than the radius (r) of the burr 25 for purposes, such as to reduce the aggressiveness of material removal. By setting offset (d2) less than the burr radius (r), milling time increases, but a less aggressive cut is provided as well as potentially reduced burr chatter, reduced motion of the anatomy, etc.

The value of offset (d2) could be different in different directions. It may be desirable to have one value for horizontal cuts and another for vertical cuts. There may also be a changing value for different density areas.

The operator could also vary speed and feed during the procedure to optimize the cutting. This could be done if tool chatter was detected. The offset (d2) could be modified during the procedure to improve efficiency for remaining cuts.

The software program 80 can identify "islands" in the resection face (RF) by comparing geometric features of the resection face (RF) to the offset (d2). In one example, the software program 80 computes a width of the perimeter edge 110 and/or boundary and evaluates whether the width is less than two times the offset (d2). If so, then there is no need for an interior path segment 112'. Alternatively, if the width is greater than two times the offset (d2), then the interior path segment 112' should be generated to address the "island. This technique is not limited to the specific values listed in this example.

The interior path segment 112' is generated at the predetermined distance and may have any features of the perimeter segment 110' and/or boundary segment 111' (e.g., open or closed, and any shape). This offsetting process can be repeated for nesting any number of interior segments 112'.

The perimeter segment(s) 110' and/or boundary segment(s) 111' may be milled before milling of the interior path segment(s) 112'. Alternatively, the perimeter segment(s) 110' and/or boundary segment(s) 111' may be milled after milling of the interior path segment(s) 112'. For example, for femoral canal prep for a total hip arthroplasty, milling may begin on the inside of the femoral canal such that interior portions are milled first and then milling works its way out to the perimeter. These techniques may be applied along successive sections (S) with differing offset (d2) values on and within each section (S). There may be multiple offset (d2) parameters depending on the number of nested islands (which could be based on bone density). Similarly, offset (d2) could be a function of island size. For some sections (S), (d2) may be varied. Alternatively, the offset (d2) may be disregarded and the islands may be ignored for certain sections (S), but not others.

The interior path segment 112' can be addressed using geometrical techniques other than those described herein.

iv. Transition Segments

With continued reference to FIGS. 8, 9, 12, one or more transition segments (t) are designed to connect the perimeter segment 110' and/or boundary segment 111' and the interior path segment 112'. The transition segment (t) can also connect two interior segments 112'. The transition segment (t) is bounded within the section (S), and more specifically, the resection face (RF). The transition segments (t) may be planar or non-planar.

The transition segment (t) can be designed to be tangential to adjoining path(s). The transition segment (t) may be curved or linear. In either case, tangential design provides smooth transitions between the paths and avoids sudden direction changes that could affect the milling accuracy.

2. Further Examples of Section Paths

In summary, the section path (SP) is a combination of any perimeter segments 110', boundary segments 111' interior segments 112' and transition segments (t).

One example of a section path (SP) showing each of these features is shown in FIG. 12. In FIG. 12, the section path (SP) is shown without reference to the resection face (RF). The numerals identified along each segment indicate the sequential order that the tool 20 traverses along the section path (SP) in this example.

Here, the closed outer loop of the section path (SP) is formed by one contoured perimeter segment 110' and two linear boundary segments 111'. The section path (SP) begins at 1a along the boundary segment 111', continues along the perimeter segment 110', and returns to the boundary segment 111' to close the outer loop (see 1b, 1c). Points (SP-START) and (SP-END) may or may not be coincident. For example, it may be more efficient to have a space identified at the transition areas. The section path (SP) comprises a transition segment (t) at 2, which nearly tangentially connects 1c and interior segments 112' forming an inner loop 3a-3c. To predominately close the inner loop, the path may move along interior segment 112' at 3a, 3b, 3c. At 4, a second transition segment (t) tangentially transitions from the inner loop 3c to an island formed by path segment 5. After the loop is closed for the island, the path continues through segment 6, a third transition segment (t) that is nearly tangential. Segments 4 and 6 are in opposite directions but do not follow the same route. At segment 7, the path transitions to the other side to address a second island. A fourth tangential transition segment (t) is provided at 8. Segment 9 is provided to remove the second island. The path returns at segment 10, which is the same segment as 8, but opposing direction. The path returns to the start by segment 11, which is the same segment as 2, but opposing direction.

The software program 80 could implement an algorithm to compute tool 20 velocity and speed along with the tool path 100. Alternatively, the software program 80 could compute parameters of interest (e.g., voxel brightness intersected by the path, direction changes, or other parameters) that could be used downstream to compute feed rate or acceleration of the tool 20. Examples of drastic changes in the milling path 100 that may require feed rate changes are changes seen along segments 5 and 9 in FIG. 12.

FIG. 12 provides an example for purposes of illustration. The section path (SP) can be different from that shown.

With continued reference to the examples of FIGS. 7-11, additional features of the section path (SP) are further understood with reference to the following examples. In the following examples, it is assumed for simplicity that the footprint (FP) is a planar face and that the allowed area (AA), the offset boundary (O), and hence, the inner area (IA) have simpler shapes. Further, in these examples, the footprint (FP) is demarcated by the border (shown in bolded dash line) of the allowed area (AA) that intersects the resection face (RF). As will be seen in these examples, the footprint (FP) is different for different resection face (RF) geometries.

The offset boundary (O) is spaced apart from border of the allowed area (AA) by the offset distance (d) equal to the radius (r) of the burr 25. The portion of the offset boundary (O) that follows the footprint (FP) is the offset footprint (OFP).

The examples below are for partial knee replacement, specifically, and using an inlay component for the distal femur anatomy. Of course, depending on the type of situation, the planning of the section path (SP) may be different from the example shown.

Certain references are made below to "plateau", "peak", "slope", "valley", and "overhang" for the resection faces (RF). While these terms provide some simplified context to understand the nature of the resection faces (RF), these terms are not intended to limit the technical scope of the solutions provided herein. It may be possible to use the techniques described below for any one or more geometries of the resection faces (RF) described herein or not.

i. Plateau

In a first case, as shown in FIG. 7, the section path (SP) is designed to address the resection face (RF) having a "plateau" shape. The inner area (IA) demarcated by the offset boundary (O) and the anatomical volume (A) do not overlap and have no common points. In other words, no part of the offset boundary (O) or offset footprint (OFP) intersect the resection face (RF).

In this example, if milling were to proceed along the perimeter edge 110 of the resection face (RF), the burr 25 would overcut the footprint (FP). Accordingly, to mill the footprint (FP) accurately and without over-resecting, the section path (SP) is designed with a single boundary segment 111" coinciding with the portion of the offset footprint (OFP). The boundary segment 111" is "floating" because it does not overlap the resection face (RF). The floating boundary segment 111" is an open-ended segment. Here, the floating boundary segment 111" comprises two ends that are floating. This single floating boundary segment 111" is sufficient to remove the resection face (RF).

ii. Peak

In a second case, as shown in FIG. 8, the section path (SP) is designed to address the resection face (RF) having a "peak" shape. The inner area (IA) demarcated by the offset boundary (O) and the anatomical volume (A) overlap. Hence, the offset boundary (O) intersects the resection face (RF). More specifically, the entire offset footprint (OFP) overlaps the resection face (RF). In this example, the section path (SP) includes a contoured perimeter segment 110' coinciding with the contoured upper edge 110 of the resection face (RF). The section path (SP) further includes a boundary segment 111' coinciding with the offset footprint (OFP). The perimeter segment 110' and the boundary segment 111' are connected such that the section path (SP) is a closed loop. The pass along the perimeter segment 110' and the boundary segment 111' is not sufficient to remove the entire portion of the resection face (RF) contained in the inner area (IA). Hence, a transition segment (t) is defined from the boundary segment 111' to an interior segment 112'. The interior segment 112' itself forms a closed loop design to remove expected "island" left in the inner area (IA).

iii. Slope

In a third case, as shown in FIG. 9, the section path (SP) is designed to address the resection face (RF) having a "slope". The inner area (IA) demarcated by the offset boundary (O) and the anatomical volume (A) once again overlap. This example is similar to the previous example shown in FIG. 8 because it includes the contoured perimeter segment 110' and boundary segment 111' forming a closed loop as well as the transition segment (t) leading into the interior segment 112' forming a nested closed loop.

However, in this example, only a portion of the offset footprint (OFP) overlaps the resection face (RF). Hence, if milling were to proceed using only the two closed loops, there would be a portion (in the lower left corner) of the resection face (RF) that would be beyond the radius (r) of the burr 25. Accordingly, to reach this portion, the section path (SP) is designed with a floating boundary segment 111" coinciding with the portion of the offset footprint (OFP) that does not overlap the resection face (RF). The floating boundary segment 111" has one open end. In other words, the floating boundary segment 111" comprises a proximal end connected to the closed loop and a distal end that is floating.

Despite only a portion of the offset footprint (OFP) overlapping the resection face (RF), it is worth noting that offset footprint (OFP) extends along the entire width of the lower horizontal segment of the offset boundary (O). This is because the exposed slope of the resection face (RF) exhibits prominent enough overlap with the allowed area (AA). In other words, the section path (SP) needs to extend along the entirety of the lower horizontal segment to sufficiently remove the resection face (RF).

iv. Valley

Figure 10:
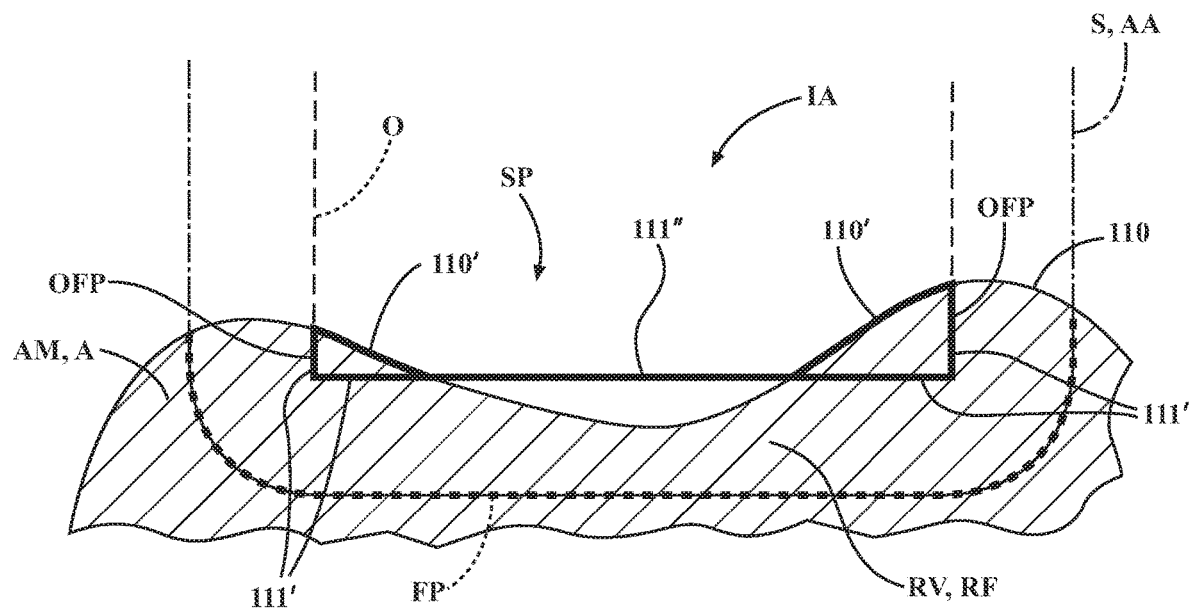
FIG. 10 is one example of the section path defined for milling the resection face having a valley, as shown.

In a fourth case, as shown in FIG. 10, the section path (SP) is designed to address the resection face (RF) having a "valley" shape. The inner area (IA) is demarcated by the offset boundary (O) and the anatomical volume (A). This example is similar to the previous example shown in FIG. 9 because only a portion of the offset footprint (OFP) overlaps the resection face (RF). Hence, the section path (SP) is designed again with the floating boundary segment 111" coinciding with the portion of the offset footprint (OFP) that does not overlap the resection face (RF).

However, unlike the examples of FIGS. 7 and 9 where the floating boundary segment 111" is open-ended, the floating boundary segment 111" here is a closed-ended segment. Mainly, the inner area (IA) intersects the resection face (RF) at two distinct (disjointed) regions. A contoured perimeter segment 110' and a boundary segment 111' are defined to form closed loop for each region. A first end of the floating boundary segment 111" is connected to one closed loop and second end of the floating boundary segment 111" is connected to the other closed loop.

The scenario in FIG. 10 may provide an indication for the software program 80 to split the path. When islands are detected, the path 100 may split to progress through all slices for that island then return to cut the slices for the other island. Cutting one island at a time may be favored over cutting one level of all islands at the same time. The program 80 may compute the path to finish one island before returning to cut the next.

The path 100 could also eliminate the inner loop if the remaining cuts are expected to pass fully through the bone. There may be locations where the path can progress through the bone and one large (e.g., center piece) be removed at the completion. The location and size of the tool shaft may be considered when making this type of path.

v. Overhang

Figure 11:
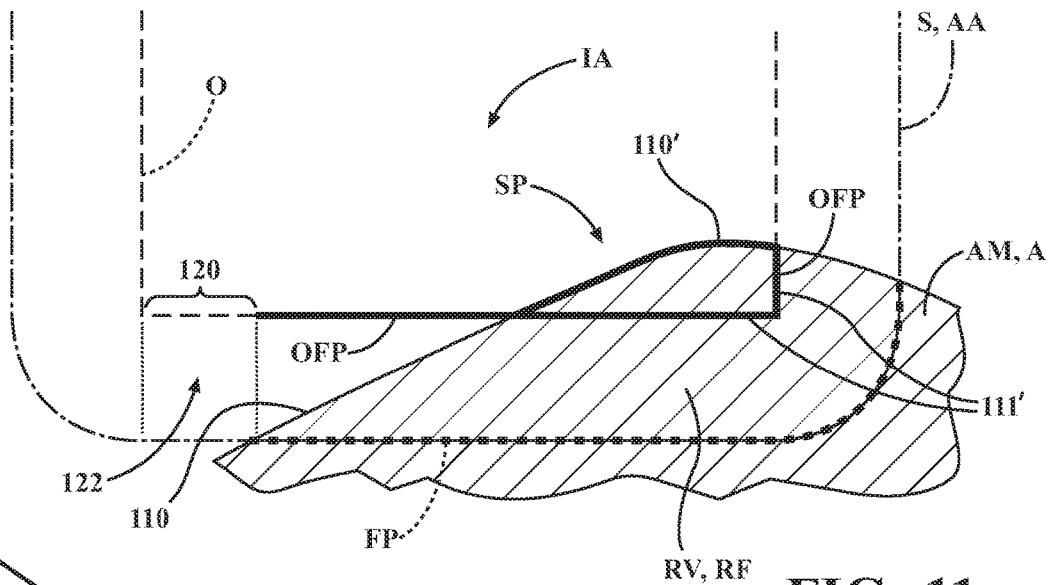
FIG. 11 is one example of the section path defined for milling the resection face with a slope and further requiring a milling in an overhang portion, as shown.

In a fifth case, as shown in FIG. 11, the section path (SP) is similar to the example of FIG. 9 in that the section path (SP) is designed to address the resection face (RF) having a "slope". Moreover, only a portion of the offset footprint (OFP) overlaps the resection face (RF) leaving the open-ended floating boundary segment 111" extending from the closed loop. Similarly, the section path (SP) extends along the entire offset footprint (OFP).

However, in this example, the exposed slope of the resection face (RF) exhibits less prominent overlap with the allowed area (AA) as compared with FIG. 9. As a result, the offset footprint (OFP) is truncated and extends along only a portion of the entire width of the lower horizontal segment of the offset boundary (O). Accordingly, the section path (SP) needs to extend along only a portion of the lower horizontal segment to sufficiently remove the resection face (RF). The remaining portion of the lower horizontal segment of the offset boundary (O) is not part of the offset footprint (OFP) and is called an overhang portion 120.

The area defined by the width of the overhang portion 120 and by the length between the overhang portion 120 and the boundary of the allowed area (AA) is referred to as the overhang area 122. The overhang area 122 comprises no part of the resection face (RF) and is named so because the overhang area 122 "hangs over" a portion of the anatomical volume (A). Notably, the overhang area 122 is in the allowed area (AA) in FIG. 11 because the allowed volume (AV) is often defined based on the implant geometry. Trimming the overhang portion 120 is still beneficial to reduce the length of milling path 100 by removing 'air cutting' that is not removing any required bone/tissue in the resection volume (RV).

Overhang portions 120 and overhang areas 122 may exist in ways other than those shown herein, and the techniques described can address any given overhang situation. Moreover, the reference to the lower horizontal segment of the offset boundary (O) is defined relative to the Figures. Of course, depending on the specific geometry, such segments can be oriented any direction.

F. Lead-In Segment

Figure 14B:
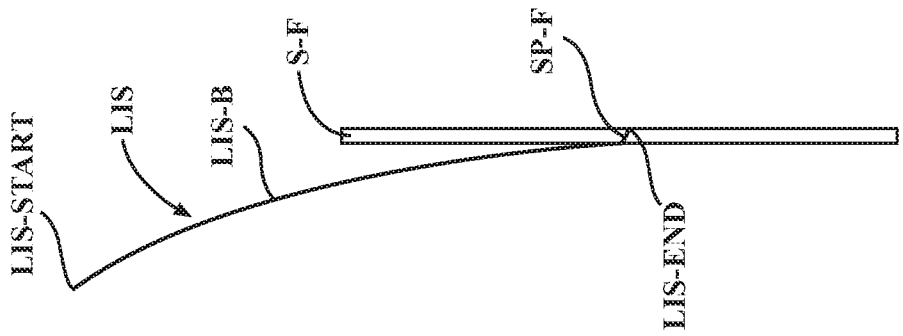
FIGS. 14A and 14B are respective front and side views of a lead-in segment of the milling path designed to smoothly guide the tool to the first section path.
Figure 14A:
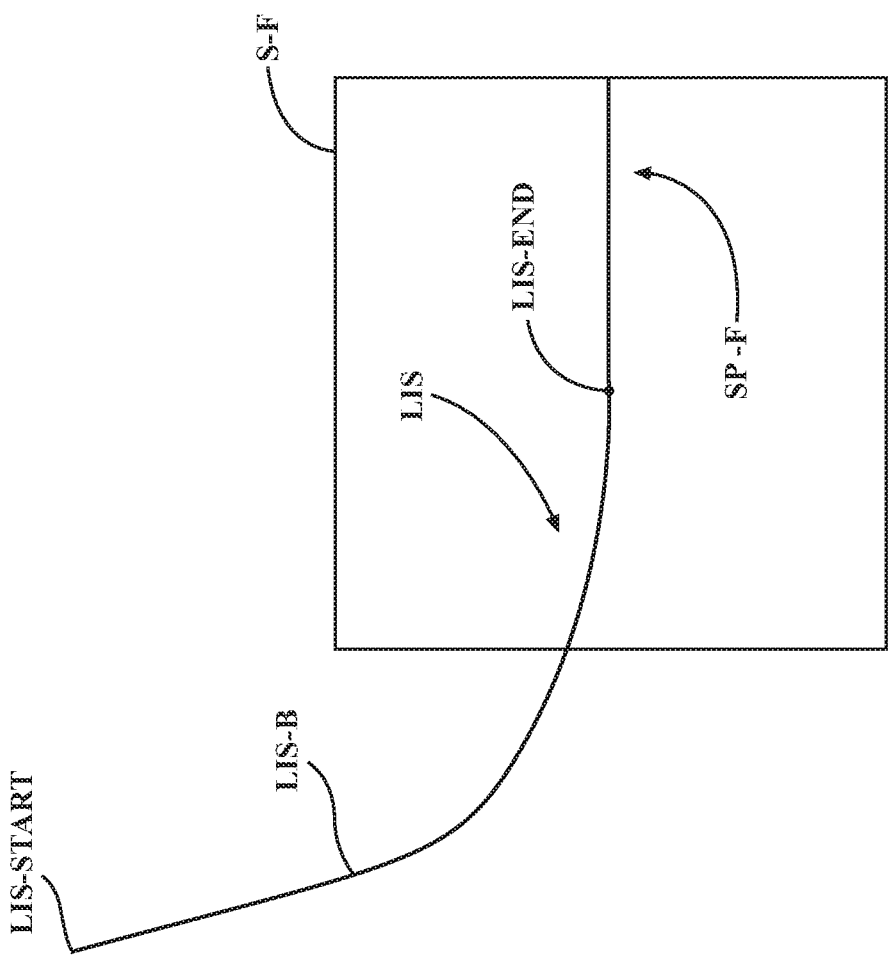

As described above, the milling path 100 comprises the first section path (SP-F) defined relative to the first section (S-F). Although milling predominately occurs with respect to the section paths (SP), the software program 80 is configured to generate a lead-in segment (LIS) for guiding the tool 20 to the first section path (SP-F), as shown in FIGS. 14A, 14B and 15. The lead-in segment (LIS) can be understood as the first segment of the milling path 100.

Unlike the section paths (SP), the lead-in segment (LIS) is not bound by the section (S). Instead, the lead-in segment (LIS) is a non-planar freeform curve.

The lead-in segment (LIS) comprises a starting point (LIS-START) and an ending point (LIS-END). According to one example, the starting point (LIS-START) of the lead-in segment (LIS) is defined relative to and/or proximate to the starting point (RS-START) of the reference spline (RS). For example, the starting point (LIS-START) may share (X, Y) coordinates of the reference spline starting point (RS-START)), but may have a different (Z) coordinate. In other words, the starting point (LIS-START) may be elevated directly above the reference spline starting point (RS-START).

Other positioning configurations for the starting point (LIS-START) are possible for providing a suitable starting position for the milling path 100 to maximize milling efficiency and without adverse effects to the anatomical volume (A). LIS-START might be chosen at a designated safe/convenient anatomical location for the surgeon, from which the tool 20 can be guided in to the first section path (SP-F). Alternately, LIS-START might be set to the current position of the TCP at the time that the milling operation is initiated, for which case lead-in segment (LIS) would be calculated on-the-fly.

The ending point (LIS-END) of the lead-in segment (LIS) is designed to be coincident to the starting point (SP-START) of the first section path (SP-F). As such, the milling path 100 seamlessly transitions from the lead-in segment (LIS) to the first section path (SP-F).

A body (LIS-B) of the lead-in segment (LIS) is defined between the starting and ending points (LIS-START, LIS-END). The body (LIS-B) is 3-dimensional and is designed to move the tool 20 towards the resection volume (RV). The lead-in segment (LIS) may be a line segment or freeform curve.

Milling by the tool 20 may or may not occur while the tool 20 traverses the body (LIS-B) of the lead-in segment (LIS).

The lead-in segment (LIS) may be designed in various ways. The software program 80 defines the lead-in segment (LIS) such that the entirety of the lead-in segment (LIS) is disposed within the allowed volume (AV), where present. Where the offset boundary (O) is present, the entirety of the lead-in segment (LIS) is disposed within the inner volume (IV) defined by the offset boundary (O). Understood differently, the shortest distance between the lead-in segment (LIS) and the boundary of the allowed volume (AV) is greater than the offset distance (d), e.g., the radius (r) of the burr 25.

The entirety of the lead-in segment (LIS) need not be disposed in the resection volume (RV). In other words, the lead-in segment (LIS) can be partially or entirely outside of the resection volume (RV).

In one example, as shown in FIGS. 14A and 14B, the lead-in segment (LIS) is tangential to the first section path (SP-F). The lead-in segment (LIS) is designed according to a curved function, such as a polynomial or spline function. The first portion of the first section path (SP-F) is tangent to the lead-in segment (LIS) at the ending point (LIS-END).

Additionally or alternatively, the lead-in segment (LIS) can be tangential to an exterior surface of the anatomical volume (A) or resection face (RF). The geometric engine 72 can identify the profile of the exterior surface in the first section (S-F), for example. The exterior surface can be curved or planar.

Further still, the lead-in segment (LIS) can be designed such that it is tangential to the reference spline (RS). The geometric engine 72 can identify the profile of the reference spline (RS) near the first section path (SP-F). The lead-in segment (LIS) may dip towards the reference spline (RS) such that the lead-in segment (LIS) and the reference spline (RS) are tangent at a common point.

Such designs for the lead-in segment (LIS) reduce chatter and tool forces when the burr 25 first penetrates the anatomical volume (A) through cortical bone, provide a smooth transition to the first section path (SP-F) and thereby avoid plunge cuts. The feed rate of the tool 20 can be controlled during the lead-in segment (LIS) to further ensure a smooth transition. The lead-in segment (LIS) may have designs other than those described herein and specifically shown in the figures.

G. Transition Segments

With the section paths (SP) and lead-in segment (LIS) described, the following section addresses how the milling path 100 transitions from one section path (SP) to the next.

1. Design Overview

Figure 13:
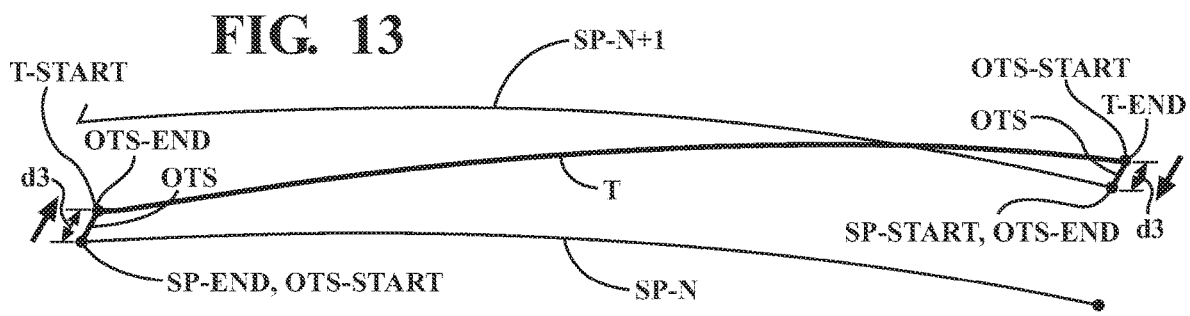
FIG. 13 is one example of a transition segment and offset transition segments of the milling path that transition the milling path from one section path to the next.

The software program 80, with the assistance of the geometric engine 72 and path generator 68, is configured to generate one or more transition segments (T) between two section paths (SP), as shown in FIGS. 13 and 15. Specifically, each transition segment (T) connects successive section paths (SP) to one another.

The number of transition segments (T) will depend on the number of section paths (SP). In one example, the number of transition segments (T) is one less than the number of section paths (SP).

As described, each section path (SP) has the starting point (SP-START) and the ending point (SP-END). Each transition segment (T) has a starting point (T-START) and an end point (T-END). A body of the transition segment (T) extends between the starting point (T-START) and end point (T-END).

The software program 80 generates each transition segment (T) by connecting the ending point (SP-END) for the section path (SP-N) of one section to the starting point (T-START) of the transition segment (T). The body of the transition segment (T) extends to the end point (T-END). The end point (T-END) of the transition segment (T) connects to the starting point (SP-START) of the next section path (SP-N+1) along the reference spline (RS).

Connection between transition segment (T) and the section path (SP) may be direct. Alternatively, as described below, there may be intermediate segment(s) between the transition segment (T) and the section path (SP).

Similar to the lead-in segment (LIS), the transition segment (T) is not bound by section (S). Instead, the transition segment (T) is a planar or non-planar segment transitioning between sections (S). The transition segment (T) may be a linear or a non-linear curve. In some examples, it may be desirable for the transition segment (T) to be a curve that is tangent to the ending point (SP-END) of the previous section path (SP), at (T-START), and tangent to the next sections path (SP) starting point (SP-START), at (T-END).

The body of the transition segment (T) may be defined with respect to the footprint (FP). For example, the software program 80 can connect the ending point (SP-END) of section path (SP-N) to the starting point (SP-START) of the successive section path (SP-N+1) using a straight line. The geometric engine 72 can create a plane through this line. In some instances, the plane can be orthogonal or nearly orthogonal to a segment of the reference spline (RS) between adjacent sections (S). The footprint (FP) is intersected by the plane to determine the transition curve. The exposed profile of the footprint (FP) is identified and the body of the transition segment (T) can be made to correspond to the exposed profile (i.e., the intersection curve of the plane and the footprint FP).

As will be described below, the transition segment (T) may be at various levels relative to the footprint (FP) to avoid damaging the anatomical volume (A). For example, the transition segment (T) may be elevated to the level of the offset footprint (OFP) boundary or to the level of the perimeter boundary. Alternatively, the transition segment (T) may not be elevated and may be coincident with the footprint from the starting point (T-START) to the end point (T-END).

The transition segment (T) may be entirely or partly within any of the allowed volume (AV), inner volume (IV), and/or resection volume (RV). The transition segment (T) may have configurations or shapes other than those described herein.

Milling by the tool 20 may or may not occur while the tool 20 traverses the body of the transition segment (T). If milling will not occur during the transition, it is important that the elevation of the transition segment is such that the tool 20 does not interact with the resection volume (RV) during the transition between adjacent sections (S).

2. Offset (Lifted) Transition

In some instances, the transition segment (T) may be offset or "lifted" from the footprint (FP). In particular, lifting the transition segment (T) from the footprint (FP) reduces the amount of material milled while traversing the transition segment and hence avoids overly aggressive material removal of the anatomical volume (A). In turn, the techniques described herein improve the quality of the milling result.

With reference to FIG. 13, the software program 80 generates one or more offset transition segments (OTS). Each offset transition segment (OTS) comprises a start point (OTS-START) and end point (OTS-END). In the example shown, there are two offset transition segments (OTS) associated with two ends of one transition segment (T). Alternatively, there may be one offset transition segment (OTS) associated with only one side of the transition segment (T).

The software program 80 is configured to determine or receive input specifying a transition-offset (d3). The transition-offset (d3) defines the distance between start point (OTS-START) and end point (OTS-END). In other words, the transition-offset (d3) defines how high to lift the transition segment (T). In one example, (d3) may be computed based on the maximum depth of the resection volume (RV) along the body of the transition segment (T), such that minimal or non-excessive material is removed during the transition. The transition-offset distance (d3) may be different or the same on opposite sides of the transition segment (T).

With the assistance of the geometric engine 72, the software program 80 generates each offset transition segment (OTS) with a length defined by the transition-offset (d3). As shown in the example, the program 80 connects the start point (OTS-START) of the first offset transition segment (OTS) (shown on the left) to the ending point (SP-END) for the section path (SP-N) of one section. This offset transition segment (OTS) extends in a direction that is opposite or points away from the reference spline (RS). The offset transition segment (OTS) may be nearly orthogonal to the footprint (FP). The offset transition segment (OTS) has the effect of creating a lift for the transition segment (T). The end point (OTS-END) of the offset transition segment (OTS) connects to the starting point (T-START) of the transition segment (T).

The transition segment (T) body follows a slight curvature, in this example, corresponding to a rough offset curve of the footprint (FP) surface. Alternately, the curvature of the transition segment (T) body could be based on the profile of the perimeter of the resection volume (RV) (i.e., bone/tissue outer surface), or based on tangency considerations on either end of the transition segment. The end point (T-END) of the transition segment (T) connects to the start point (OTS-START) of the second offset transition segment (OTS).

The end point (OTS-END) of the second offset transition segment (OTS) connects to the starting point (SP-START) of the next section path (SP-N+1) along the reference spline (RS). This second offset transition segment (OTS) extends in a direction towards the reference spline (RS), or towards the (FP) and almost orthogonal to the (FP). This may have the effect of creating a lowering for the transition segment (T). This technique can be repeated and/or modified for any given transition segment (T) along the milling path 100.

In some examples, the offset transition segments (OTS) are bounded within sections (S), and more specifically, to the same section (S) by which binds the section path (SP) connected to the offset transition segments (OTS). Alternatively or additionally, the offset transition segments (OTS) can be partially bound by the section (S) and partially extending therefrom. Said differently, the "lift" or the "drop" provided by the offset transition segments (OTS) can be planar or curved trajectories. The offset transition segment (OTS) can be smoothly tapered to gradually enter deeper into the resection volume (RV), to avoid an inadvertent plunge cut with the burr when starting the next section path (SP).

The offset transition segments (OTS) may be entirely or partly within any of the allowed volume (AV), inner volume (IV), and/or resection volume (RV). The offset transition segments (OTS) may have configurations or shapes other than those described herein.

H. Lead-Out Segment

As described above, the milling path 100 comprises the last section path (SP-L) defined relative to the last section (S-L). In some cases, the milling path 100 can finish at the end of the last section (S-L). Optionally, however, the software program 80 is configured to conclude the milling path 100 with a lead-out segment (LOS), as shown in FIG. 15, for example. When present, the lead-out segment (LOS) is the last segment of the milling path 100. The lead-out segment (LOS) is designed for guiding the tool 20 away from the last section path (SP-L) and the anatomical volume (A) to return the tool 20 to a safe/convenient location for the surgeon to access. In such instances, the lead-out segment (LOS) is generally not designed to remove material.

The lead-out segment (LOS) comprises a starting point (LOS-START) and an ending point (LOS-END). The starting point (LOS-START) of the lead-out segment (LOS) is connected and coincident to the ending point (SP-END) of the last section path (SP-L). As such, the milling path 100 seamlessly transitions from the last section path (SP-L) to the lead-out segment (LOS).

A body (LOS-B) of the lead-out segment (LOS) is defined between the starting and ending points (LOS-START, LOS-END). The body (LOS-B) is designed to move the tool 20 in along any suitable path. Similar to the lead-in segment (LIS), the lead-out segment (LOS) is not bound by the section (S). Instead, the lead-out segment (LOS) is a line or a smooth freeform curve. The lead-out segment (LOS) may or may not intersect any one or more of the sections (S). Milling by the tool 20 may or may not occur while the tool 20 traverses the body (LOS-B) of the lead-out segment (LOS).

According to one example, the ending point (LOS-END) of the lead-out segment (LOS) is defined relative to and/or proximate to the starting point (RS-START) of the reference spline (RS). In this regard, the ending point (LOS-END) of the lead-out segment (LOS) may be defined proximate to the starting point (LIS-START) of the lead-in segment (LIS). The ending point (LOS-END) may be located past the first section (S-F) of the first section path (SP-F). In one example, the ending point (LOS-END) may be located in the inner volume (IV) defined by the offset boundary (O).

In such instances, the lead-out segment (LOS) returns back towards the first section path (SP-F). For knee arthroplasty, this return path may directionally be from anterior to posterior. The lead-out segment (LOS) may return by following a trajectory projected relative to (spaced above) the reference spline (RS), or by following the reference spline (RS) itself, in reverse.

Other positioning configurations for the ending point (LOS-END) are possible for providing a suitable ending position for the milling path 100 to minimize milling time and without adverse effects to the anatomical volume (A).

The body of the lead-out segment (LOS-B) may be designed in various ways. The software program 80 defines the lead-out segment (LOS) such that the entirety of the lead-out segment (LOS) is disposed within the allowed volume (AV), where present. Where the offset boundary (O) is present, the entirety of the lead-out segment (LOS) may be disposed within the inner volume (IV).

The entirety of the lead-out segment (LOS) need not be disposed in the resection volume (RV). In other words, the lead-out segment (LOS) can be partially or entirely outside of the resection volume (RV).

As can be understood from the examples of FIGS. 14A and 14B relating to the lead-in segment (LIS), the lead-out segment (LOS) can be tangential to the last section path (SP-L). The last portion of the last section path (SP-L), i.e., leading up to the ending point (SP-END), may be understood as a tangent line. The lead-out segment (LOS) is designed according to a curved function, such as a polynomial or spline function. The last portion of the last section path (SP-L) is tangent to the lead-out segment (LOS) at the ending point (SP-END).

The lead-out segment (LOS) can be tangential to the exterior surface of the anatomical volume (A) or resection face (RF), similar to the lead-in segment (LIS).

Such designs for the lead-out segment (LOS) reduce burr chatter on contact with the last cortical bone portion, provide a smooth transition from the last section path (SP-L) and avoid disruptions to the milled surface by the tool 20 during the exit.

There may be instances where the lead out segment (LOS) is the direct connection of the end point of one path 100 and the start point of a successive path 100' (effectively covering path concatenation).

The lead-out segment (LOS) may have designs other than those described herein and specifically shown in the figures.

J. Milling Example

With continued reference to FIG. 15, one example of the milling path 100 is provided including each of the aforementioned features. The milling path 100 shown here is only one example. The techniques described herein may generate the milling path 100 with less or more features than shown in FIG. 15. This example milling path 100 is designed for removal of the resection volume (RV) to accommodate a unicondylar onlay implant for femur distal as part of a partial knee replacement procedure. The arrows shown illustrate the direction of the tool 20 along the path 100.

The tool 20 initially begins moving along the lead-in segment (LIS) until the tool 20 tangentially reaches the starting point of the first section path (SP-F). The tool 20 follows transition segments (T) connecting successive section paths (SP). The tool 20 is elevated during certain transition segments (T) by following the offset transition segments (OTS).

The tool 20 performs the majority of milling through the section paths (SP) and transitions (T). For many of the section paths (SP), the tool 20 follows one or two perimeter segments 110' or boundary segments 111'. In the areas where the resection volume (RV) is thicker, the tool 20 follows more complex features for removing islands, such as interior path segments 112' and transition segments (t). After completing the last section path (SP-L), the tool 20 follows the lead-out segment (LOS). The tool 20 moves along the lead-out segment (LOS) thereby returning near the first section path (SP-F) along a trajectory following above the reference spline (RS). Near the end of the lead-out segment (LOS) the tool 20 moves away from the anatomical volume (A), thereby concluding milling.

Milling by the tool 20 may be implemented in various ways along any segment of the path 100. For example, milling may be "conventional" or "climb" milling. With "conventional" milling, the direction of milling path is against the rotation of the burr 25. FIG. 12 shows an example of a planar conventional milling path. With "climb" milling, the direction of milling path is with the rotation of the burr 25. For some applications, climb milling may provide a superior surface finish since the burr 25 tends to throw chips behind its milling path and avoids re-cutting.

In one example, "climb" milling is used for all segments of the milling path 100, with the exception of the transition segments (T). With "conventional" milling used for transition segments, lifting the transition segment (T) from the footprint (FP) reduces the amount of material milled while traversing the transition segment and hence optimizes the surface finishing of the anatomical volume (A). In turn, the techniques described herein improve the quality of the milling result while accommodating two different types of milling approaches.

The directions for the milling path 100 in FIG. 12 or 15 may be different from that shown. Moreover, climb or conventional milling may be utilized for any of the segments of the milling path 100 described herein.

K. Graphical User Interface

The software program 80 is optionally configured with instructions, which when executed by one or more of the processors 70, optionally implements a graphical user interface (GUI). In one example, the GUI 96 is implemented by the clinical application 74. The GUI 96 can be displayed on any of the displays 38 of the system 10 and can receive input from any of the input devices 40, 42.

The GUI 96 may provide an interface to enable the user to selectively design the milling path 100 and/or input control parameters of the milling path 100. In other examples, however, the surgeon would not directly design the path 100 or specify these path parameters. Rather, the surgeon would use the GUI 96 to position the implant relative to the anatomy, or to potentially define the resection volume (RV).

The GUI 96 may provide visualization for viewing or design of any of the aforementioned features of the milling path 100. Examples of the parameters that can be adjusted using the GUI 96 include, but are not limited to, tool parameters, path parameters, and milling parameters. The parameters can be designed offline and included as part of the implant plan, and the user (surgeon) views/approves the plan prior to execution.

Examples of tool parameters include any settings relating to the tool 20, such as setting a geometric feature of the tool 20. The geometric feature can be the type of energy applicator 24, etc. For example, where the energy applicator 24 is the burr 25, the GUI 96 enables inputting of the radius (r) of the burr 25. Using this parameter, the software program 80 can auto-generate various features described above, such as the offset distance (d), the distance (d1) between sections (S) along the guide (G), or the like. Alternatively, the user may not enter these parameters directly into the GUI 96, but rather the system would allow the parameters to be configured in the software via configuration file, automatically read from built-in memory in the energy applicator, tool, or burr, etc.

Examples of path parameters include any settings that relate to planning or generation of the milling path 100. Such path parameters may include for example, defining the offset distance (d), the distance (d1) between sections (S) along the guide (G), the offset (d2) to define the interior path segments 112', the transition-offset (d3), any of the starting and/or ending points described herein, the trajectory of any segment described herein, and/or features, properties, or types (curve, plane, etc.) of the reference guide (G), Examples of milling parameters include any settings that relate how to milling is executed along the path 100. Such parameters may include feed rate (tool 20 speed along the path), burr 25 rotation speed, tool 20 orientation, etc. The GUI 96 can also enable the user to select the milling type. In other words, the user can select conventional or climb milling and to associate such milling with any segment of the path 100.

Additional parameters include definition of the resection volume (RV), desired surface finish/accuracy, desired trade-off between accuracy and milling time (may be a different trade-off depending on whether cemented or press-fit implants are being used). Any of the parameters described herein may be pre-defined settings may be provided by the software 80 based on offline engineering characterization of cutting performance, etc. The parameters may be different based on different selected procedures or may be computed indirectly based on information provided by the user.

The GUI 96 may have features other than those described herein. In particular, the GUI 96 may take clinical or high-level input from the surgeon, and use this information to compute the lower-level settings used for generating the milling path 100. In other words, the settings may be specified indirectly based on the user input.

The GUI 96 is optional, and the path generation techniques described herein can take place without user interaction. In such instances, the parameters described above, such as the tool parameters, may be stored in memory and retrieved from memory. Milling parameters can be adapted based on imaging data, e.g. bone density measures. In denser bone, it could be of advantage to reduce the distance between the sections, or the distance between the offset paths. The burr 25 speed could also be influenced by such a measure.

Several embodiments have been described in the foregoing description. However, the embodiments discussed herein are not intended to be exhaustive or limit the invention to any particular form. The terminology, which has been used, is intended to be in the nature of words of description rather than of limitation. Many modifications and variations are possible in light of the above teachings and the invention may be practiced otherwise than as specifically described.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A computer-implemented method for generating a milling path for a bone, the computer-implemented method comprising:
    obtaining a virtual model of the bone, a resection volume defined relative to the virtual model of the bone, and a reference guide defined with respect to the resection volume;
    producing a plurality of section planes being successively arranged along the reference guide, and each section plane intersecting the reference guide and intersecting the resection volume;
    generating a section path within each section plane and being defined relative to the resection volume;
    generating transition segments for connecting section paths of section planes; and
    combining the section paths and the transition segments to generate the milling path.

2. The computer-implemented method of claim 1, comprising:
    obtaining an allowed volume that is intersected with the virtual model of the bone; and
    obtaining the resection volume based on an intersection between the allowed volume and the virtual model of the bone.

3. The computer-implemented method of claim 2, comprising:
    obtaining the allowed volume having a geometry derived, in part, from a geometry of a virtual implant model; and
    obtaining the reference guide being defined based on the geometry of the allowed volume and being disposed within the allowed volume.

4. The computer-implemented method of claim 2, comprising:
    obtaining the virtual model to be of a proximal femur bone including a canal of the proximal femur bone;
    obtaining the resection volume defined relative to the canal of the virtual model of the proximal femur bone; and
    generating the milling path for enabling a tool to remove material from the canal of the proximal femur bone.

5. The computer-implemented method of claim 2, comprising:
    obtaining an offset boundary that is spaced inward from the allowed volume by a distance that is derived from a radius of a tool; and
    generating at least one section path to be at least partially coincident to the offset boundary.

6. The computer-implemented method of claim 1, comprising:
    obtaining the reference guide being derived from a surface of the resection volume.

7. The computer-implemented method of claim 1, comprising:
    obtaining the reference guide by:
    approximating a center line of the resection volume; and
    aligning the reference guide to the center line of the resection volume.

8. The computer-implemented method of claim 1, comprising:
    obtaining the reference guide to be extending, in part, beyond the resection volume.

9. The computer-implemented method of claim 1, comprising:
    producing the plurality of section planes to be parallel to one another.

10. The computer-implemented method of claim 1, comprising:
    for at least one section plane, generating the section path to be at least partially coincident to a cross-sectional perimeter of the resection volume intersecting the section plane.

11. The computer-implemented method of claim 1, comprising:
    generating at least one section path to be a closed loop.

12. The computer-implemented method of claim 1, comprising:
generating a floating path segment that connects one path segment to another path segment, wherein the floating path segment does not intersect the virtual model of the bone.

13. The computer-implemented method of claim 1, comprising:
generating each section path by generating a starting point and an ending point for each section path; and
generating one or more of the transition segments by connecting the ending point for the section path of one section plane to the starting point of the section path of another section plane being in succession.

14. The computer-implemented method of claim 1, comprising:
generating one or more of the transition segments by creating a plane between successive section planes wherein the plane is defined relative to the reference guide and the plane intersects the virtual model of the bone;
determining a contour from the intersection of the plane and a profile of the virtual model of the bone within the plane; and
generating one or more of the transition segments to be coincident to the contour.

15. The computer-implemented method of claim 1, comprising:
designating a first direction for a tool to traverse along a portion of the milling path; and
designating a second direction, opposite the first direction, for the tool to traverse along the portion of the milling path, wherein traversal in the second direction is designated to occur after traversal in the first direction.

16. The computer-implemented method of claim 1, comprising:
designating one of the section paths as a first section path to be traversed by a tool along the milling path; and
producing a lead-in segment for guiding the tool to the first section path by:
defining a starting point of the lead-in segment to be coincident to the reference guide; and
defining an ending point of the lead-in segment to be coincident to a point on the first section path.

17. The computer-implemented method of claim 1, comprising:
defining a first portion of the milling path to be removed by a tool using climb milling; and
defining a second portion of the milling path to be removed by the tool using conventional milling.

18. The computer-implemented method of claim 1, comprising:
receiving control inputs for selectively adjusting parameters for the milling path, the parameters comprising one or more of:
a geometric feature of a tool;
a distance between section planes along the reference guide; and
an offset defining a distance between closed loops in any one or more section path.

19. The computer-implemented method of claim 1, further comprising:
intra-operatively obtaining the resection volume; and
intra-operatively generating the milling path to remove the intra-operatively obtained resection volume.

20. The computer-implemented method of claim 1, comprising:
obtaining a bone density measurement of the bone; and
determining a spacing between the section planes based on the bone density measurements.

21. A non-transitory computer readable medium comprising instructions being executable by one or more processors to generate a milling path for a bone, the instructions, when executed, are configured to:
obtain a virtual model of the bone, a resection volume defined relative to the virtual model of the bone, and a reference guide defined with respect to the resection volume;
produce a plurality of section planes successively arranged along the reference guide, and each section plane intersects the reference guide and intersects the resection volume;
generate a section path within each section plane and defined relative to the resection volume;
generate transition segments to connect section paths of section planes; and
combine the section paths and the transition segments to generate the milling path.

22. The non-transitory computer readable medium of claim 21, wherein the instructions, when executed, are configured to:
obtain an allowed volume that is intersected with the virtual model of the bone; and
obtain the resection volume based on an intersection between the allowed volume and the virtual model of the bone.

23. The non-transitory computer readable medium of claim 22, wherein the instructions, when executed, are configured to:
obtain the allowed volume with a geometry derived, in part, from a geometry of a virtual implant model; and
obtain the reference guide defined based on the geometry of the allowed volume and disposed within the allowed volume.

24. The non-transitory computer readable medium of claim 22, wherein the instructions, when executed, are configured to:
obtain the virtual model to be of a proximal femur bone including a canal of the proximal femur bone;
obtain the resection volume defined relative to the canal of the virtual model of the proximal femur bone; and
generate the milling path to enable a tool to remove material from the canal of the proximal femur bone.

25. The non-transitory computer readable medium of claim 22, wherein the instructions, when executed, are configured to:
obtain an offset boundary that is spaced inward from the allowed volume by a distance that is derived from a radius of a tool; and
generate at least one section path to be at least partially coincident to the offset boundary.

26. The non-transitory computer readable medium of claim 21, wherein the instructions, when executed, are configured to:
obtain the reference guide derived from a surface of the resection volume.

27. The non-transitory computer readable medium of claim 21, wherein the instructions, when executed, are configured to:
  obtain the reference guide by being configured to:
    approximate a center line of the resection volume; and
    align the reference guide to the center line of the resection volume.

28. The non-transitory computer readable medium of claim 21, wherein the instructions, when executed, are configured to:
  obtain the reference guide to extend, in part, beyond the resection volume.

29. The non-transitory computer readable medium of claim 21, wherein the instructions, when executed, are configured to:
  produce the plurality of section planes to be parallel to one another.

30. The non-transitory computer readable medium of claim 21, wherein the instructions, when executed, are configured to:
  for at least one section plane, generate the section path to be at least partially coincident to a cross-sectional perimeter of the resection volume that intersects the section plane.

31. The non-transitory computer readable medium of claim 21, wherein the instructions, when executed, are configured to:
  obtain a bone density measurement of the bone; and
  determine a spacing between the section planes based on the bone density measurements.

32. A surgical system comprising:
  a robotic manipulator configured to support and move a cutting tool relative to a bone;
  a control system coupled to the robotic manipulator and being configured to:
    generate a milling path for the cutting tool to enable the cutting tool to remove material from the bone, wherein to generate the milling path, the control system is configured to: obtain a virtual model of the bone, a resection volume defined relative to the virtual model of the bone, and a reference guide defined with respect to the resection volume; produce a plurality of section planes being successively arranged along the reference guide, and each section plane intersects the reference guide and intersects the resection volume; generate a section path within each section plane and being defined relative to the resection volume; generate transition segments to connect section paths of section planes; and combine the section paths and the transition segments; and
    command the robotic manipulator to move the cutting tool along the generated milling path to remove the material from the bone.

\* \* \* \* \*